United States Patent [19]
Friedman et al.

[11] Patent Number: 5,330,746
[45] Date of Patent: Jul. 19, 1994

[54] DENTAL VARNISH COMPOSITION, AND METHOD OF USE

[75] Inventors: Michael M. Friedman; Amnon Sintov, both of Jerusalem, Israel

[73] Assignees: Yissum Research Development Company of the Hebrew University of Jerusalem; Petro Products Ltd., Jerusalem, Israel

[21] Appl. No.: 369,223

[22] Filed: Jun. 21, 1989

Related U.S. Application Data

[63] Continuation-in-part of Ser. No. 304,091, Jan. 31, 1989, abandoned, and a continuation-in-part of Ser. No. 189,918, May 3, 1988, abandoned.

[51] Int. Cl.$^5$ .......................... A61K 7/16; A61K 7/22
[52] U.S. Cl. .......................................... 424/49; 424/54; 424/679; 514/902
[58] Field of Search ............... 424/49, 52, 54

[56] References Cited

U.S. PATENT DOCUMENTS

| | | | |
|---|---|---|---|
| 2,984,639 | 5/1961 | Stamberger et al. | 260/32.4 |
| 3,431,208 | 3/1969 | Bailey | 252/106 |
| 4,011,309 | 3/1977 | Lutz | 424/49 |
| 4,517,173 | 5/1985 | Kizawa et al. | 424/16 |
| 4,569,837 | 2/1986 | Suzuki et al. | 424/28 |
| 4,701,320 | 10/1987 | Hasegawa et al. | 424/54 |
| 4,751,072 | 6/1988 | Kim | 424/49 |
| 4,775,525 | 10/1988 | Pera | 424/58 |
| 4,883,534 | 11/1989 | Sandham et al. | 424/407 |
| 4,911,922 | 3/1990 | Masuhara et al. | 424/81 |
| 4,925,660 | 5/1990 | Atsuta et al. | 424/81 |
| 5,160,737 | 11/1992 | Friedman et al. | 424/401 |

FOREIGN PATENT DOCUMENTS

| | | |
|---|---|---|
| 79557/87 | 4/1988 | Australia . |
| 0184389 | 6/1986 | European Pat. Off. . |
| 0264660 | 4/1988 | European Pat. Off. . |
| 0404558 | 12/1990 | European Pat. Off. . |
| 3720147 | 12/1988 | Fed. Rep. of Germany . |
| WO87/02580 | 5/1987 | PCT Int'l Appl. . |

OTHER PUBLICATIONS

Translated Abstract of Japanese patent document JP 60228410 from Dialog file 351.
English abstract of the patent family of European patent document No. EP 0 298 271 from Dialog file 351.
Translated Abstract of Japanese document JP 63044518 from Dialog file 351.
Wood, D. A., *Int. J. Pharmaceut.* 7:1-18 (1980).
Goodson, J. M. in *Medical Applications of Controlled Release, vol. II*, Langer, R. S. et al. Eds., CRC Press Inc. (1984) 115-138.
Chang, R.-K. et al., *Drug Dev. and Ind. Pharm.* 15:361-372 (1989).
Thoennes, C. J. et al., *Drug Dev. and Ind Pharm.* 15:165-185 (1989).
Goto, S. et al., *J. Microencap.* 5:343-360 (1988).

*Primary Examiner*—Thurman K. Page
*Assistant Examiner*—James M. Spear
*Attorney, Agent, or Firm*—Sterne, Kessler Goldstein & Fox

[57] ABSTRACT

The invention relates to an oral composition for plaque prevention or tooth hypersensitivity comprising either an antibacterial agent or a hypersensitivity agent embedded in a sustained release carrier such as an acrylic polymer, and a method for the use of said compositions in preventing dental caries, periodontal disease, and tooth hypersensitivity.

24 Claims, 18 Drawing Sheets

DENTAL VARNISH COMPOSITION, AND METHOD OF USE

CROSS REFERENCE TO RELATED APPLICATIONS

This application is a continuation-in-part of U.S. patent applications Ser. Nos. 07/304,091, filed Jan. 31, 1989, abandoned, and 07/189,918, filed May 3, 1988, abandoned.

FIELD OF THE INVENTION

The invention is directed to a dental varnish composition which may be used to prevent bacterial dental plaque formation, to treat dental caries and periodontal disease, or to treat patients suffering from tooth hypersensitivity.

BACKGROUND OF THE INVENTION

I. Prevention of Plaque Formation, Caries, and Periodontal Disease

The relationship between bacterial plaque and the development of periodontal disease and caries has been thoroughly established (Axelsson, P., et al., *J. Clin. Perio.* 5:133-151 (1978)). It has also been clearly shown that the bacterial flora of the gingival crevice is important in the etiology of periodontal disease (Slots, J., *J. Clin. Perio.* 6:351-382 (1979)). Therefore, treatment of periodontal and caries diseases is directed to controlling this flora.

The most widely used approach to date has been mechanical cleaning methods such as tooth brushing. Although this method has proved to be fairly successful in treating individuals, there is still a high recurrence rate. There is also the problem of motivating people to good oral hygiene habits that they will maintain throughout their lives.

Although systemic administration of antibiotics has been shown to be a useful method of controlling the subgingival flora, discontinuation of therapy will result in the return of the potential pathogens to the pockets (Genco, R. J., *J. Perio.* 52:545-558 (1981)). Long-term antibiotic therapy has been used, but the potential dangers associated with this form of treatment, which include the development of resistant strains and superimposed infections, do not warrant its serious consideration.

Antibacterial agents such as chlorhexidine and quaternary ammonium salts in the form of mouth rinses, dentifrices, solutions and gels have not proven to be successful in preventing periodontal disease (see, for example, Ciancio, S. G., et al., *Pharm. Therap. Dent.* 3:1-6 (1978)), as these agents are unable to affect the subgingival flora when administered in these forms (Goodson, J. M., et al., *J. Clin. Perio.* 6:83-92 (1979)). In addition, reported side effects of chlorhexidine, including staining and altered taste sensation, have resulted in limited usage. Attempts to reduce the staining and bitter taste by using dilute solutions and flavoring agents, respectively, have been only partially successful.

Sustained release has been reported to be achieved by embedding chlorhexidine in an ethyl cellulose polymer to form a varnish (Friedman, M., et al., *J. Perio. Res.* 17:323-328 (1982); Friedman, M., et al., *IADR Prog. and Abstr.* 59:No. 905 (1980)). This dosage form was used in the local treatment of periodontal disease (Soskolne, W. A., et al., *J. Perio. Res.* 18:330-336 (1983)) and in the treatment of plaque prevention in patients wearing orthodontic appliances (Friedman, M., et al., *J. Dent. Res.* 64:1319-1321 (1985)). A drawback to this plaque preventative system was that although plaque accumulation was decreased by the application of a varnish composed of chlorhexidine embedded in an ethyl cellulose polymer, the effectiveness of the system in decreasing plaque accumulation was present only for a period of four days subsequent to administration of the varnish. Friedman et al., (*J. Dent. Res.*, supra), concluded that "clearly the conditions in the oral cavity and the formulation used do not, at present, facilitate such prolonged prevention of plaque accumulation." These authors also suggested that by altering the varnish components and method of preparation it might be possible in clinical use to sustain the necessary level of antibacterial agent release for longer periods. No suggestion was made in this publication as to how this could be accomplished.

Other antibacterial preparations for plaque prevention have been disclosed. Gaffar (U.S. Pat. No. 4,339,430) discloses an antibacterial oral composition containing an agent such as bis-biguanidohexanes or quaternary ammonium salts, and an additive which reduces staining of dental surfaces such as copolymers of glutamic acid, tyrosine, and alanine. This preparation was reported to be applied as a mouthwash or as a toothpaste.

Wahmi (U.S. Pat. No. 4,374,824) discloses dentifrices for cleaning and preserving teeth. Disclosed were compositions comprising ginger, magnesium silicate, sodium chloride, catechu, alum, seed and shell of sweet almond, pyrethrum, gum mastic, and tobacco. It was reported that gum mastic was added to the composition to assist in the prevention of tooth decay. The disclosed compositions were intended to be in the form of toothpaste or tooth powders. This patent does not disclose the possible long-term anti-plaque effect of the compositions; further, application of the disclosed compositions two to three times per day is required for anti-plaque activity.

Mastic has been used previously for other dental purposes. U.S. Pat. No. 4,668,188 (Wolfenson, G. B.) discloses the use of a curable mastic in the production of an oral impression tray for making impressions of teeth and jaw structures. Mastics have been used in the production of dental molds (U.S. Pat. No. 4,500,288, Von Weissenfluh, H.) and as an adhesive to secure dental articulators (U.S. Pat. Nos. 4,548,581 and 4,382,787, Hoffman, R. E.). U.S. Pat. Nos. 4,532,126 and 4,428,927 (Ebert, W. R., et al.) disclose chewable, filled, one-piece soft elastic gelatin capsules, made chewable by a masticatory substance, such as a synthetic mastic.

U.S. Pat. No. 4,459,271 (Kosti, C. M.) relates to novel anti-plaque compositions for use in evaluating oral hygiene practices. In brief, the patent discloses a water-insoluble, water-immiscible dye emulsified in fine droplets or rupturable capsules. The patent discloses the use of mastic resin as well as alginates, and other gums as an insoluble media for dye dispersion. In particular, sodium carboxymethylcellulose is disclosed. Also disclosed is the possibility of incorporating antibacterial agents such as stannous fluoride into the compositions. Significantly, the Kosti patent is concerned with diagnostic rather than therapeutic applications. The patent fails to suggest compositions exhibiting long-term plaque preventive activity.

U.S. Pat. No. 3,956,480 (Dichter et al.) discloses the use of an anionic polymer to sorb a cationic germicidal polymer to a tooth surface.

A topical, sustained-release form of an antibacterial agent could help prevent the above-discussed side effects. Such a dosage form would be able to release the drug at a lower therapeutic level over a long period of time and thus might prevent the bitter taste and tooth staining.

II. Treatment of Tooth Hypersensitivity

Dental hypersensitivity, especially that arising from dentin and cementum hypersensitivity, is a frequently encountered problem in dentistry and a very troublesome clinical complaint. Hypersensitivity may occur wherever the dentin or cementum of a tooth is exposed by attrition or abrasion, or when the tooth's fine root surface is exposed by periodontal disease. In about 12% of erupted teeth, there is a developmental lack of protective covering of cementum at the cementoenamel junction. As a result, when the exposed dentin is subjected to mechanical, thermal, chemical or osmotic stimuli, the sensory nerves of the teeth become excited and a very painful response results. For example, people with hypersensitive teeth find it very painful to orally ingest certain forms of nourishment, such as liquids or foods that are hot or cold, sweet, hypertonic or contain citric acid. Everyday stimuli such as brushing the teeth may also be painful.

Many attempts have been made to control hypersensitivity of the teeth. For example, U.S. Pat. No. 3,863,006 (Hodosh, M.) describes the use of potassium, lithium or sodium nitrate; U.S. Pat. No. 4,751,072 and U.S. Pat. No. 4,631,185 (both to Kim, S.) describe the use of potassium bicarbonate and potassium chloride; U.S. Pat. No. 4,710,372 and U.S. Pat. No. 4,634,589 (both to Scheller, H. U.) describe the use of hydroxyapatite or fluorapatite; U.S. Pat. No. 4,057,621 Pashley, D. H., et al.) describes the use of an alkali metal or ammonium oxalate; U.S. Pat. No. 4,415,549 (Shah, N. B.) describes the use of strontium EDTA, fluoride and ammonium glycyrrhizzinate; and, GB patent No. 990957 (Rosenthal, M. W.) describes the use of strontium for the control of hypersensitivity. The use of strontium ions to treat hypersensitivity was also disclosed in U.S. Pat. Nos. 3,122,483, 3,988,434 and 4,224,310.

However, although clinically the most effective for reducing tooth hypersensitivity, the use of strontium salts for the treatment of hypersensitivity is disliked by patients due to the tendency of strontium salts to leave an unacceptably salty taste or metallic taste in the mouth, even when used in a toothpaste form. Another major disadvantage of strontium dentifrice is the long period of time of application which is required to achieve the clinical effect.

A topical, sustained-release form of an agent capable of controlling dental hypersensitivity could help prevent undesirable taste side effects and still treat the hypersensitive condition. Such a dosage form would be able to release the agent controlling the hypersensitivity at a lower therapeutic level over a long period of time, for example, for weeks. Sustained localized release of the hypersensitivity agent, targeted directly to the hypersensitive site, would also solve the problem of the prolonged time and application currently required to obtain clinical effectiveness with strontium.

III. Summary

The background art thus fails to identify any compositions of matter comprising a sustained-release carrier which can be used in conjunction with a bacteriocidal agent, for use as a sustained plaque preventative by humans and other animals, under conditions in which the agents have no deleterious medical side effects, and do not cause staining of the teeth. Another highly desirable characteristic not found in the art of record is that the antibacterial agent should be released from the antiplaque composition, not only in a sustained fashion, but over a sufficiently long period of time so as not to require excessive application of the composition.

The background art also fails to identify any compositions of matter comprising an effective anti-hypersensitivity agent together with a long term sustained release carrier capable of providing efficacious levels of the anti-hypersensitivity agent, for use as a hypersensitivity preventative by humans and other animals, under conditions in which the anti-hypersensitivity agents have no undesirable side effects such as changes in taste sensations.

SUMMARY OF THE INVENTION

With the above-described needs in mind, the present inventors set out to find a composition which could be adapted to contain either (1) an antibacterial agent effective against those bacteria that are responsible for plaque, dental caries or periodontal disease, or (2) an agent effective against those dental conditions responsible for tooth hypersensitivity.

The composition for treating plaque, dental caries or periodontal disease being such that the antibacterial agent can be released in a sustained, long-term fashion, and such that the antibacterial composition has the property of long-term adhesion to the gums and teeth, and such that the antibacterial composition remains plastic during the entire period of application.

The composition for treating tooth hypersensitivity being such that the active anti-hypersensitivity agent is released in a sustained, long-term fashion, without a salty or metallic taste, and such that the hypersensitivity composition has the property of long-term adhesion to the teeth, and such that the hypersensitivity composition remains plastic during the entire period of application.

With these goals in mind, the inventors have discovered a composition with these desirable characteristics, the composition comprising a degradable, but non-biodegradable, varnish. The varnish containing either an anti-plaque agent, or a metal salt or another agent to treat tooth hypersensitivity, embedded in a sustained release carrier composed of a biodegradable acrylic polymer, a hydrophilic polymer, or a combination of hydrophilic and hydrophobic polymers, in a pharmaceutically acceptable vehicle, optionally containing one or more agents such as a plasticizer (such as polyethylene glycol, dibutyl phthalate, etc.), an adhesive polymer (such as gum mastic, etc.), a cross-linking agent (such as citric acid, lysine, aspartic acid, glutaric acid, etc.), a flavorant, and/or a coloring agent.

DETAILED DESCRIPTION OF THE PREFERRED EMBODIMENTS

Figure 1:
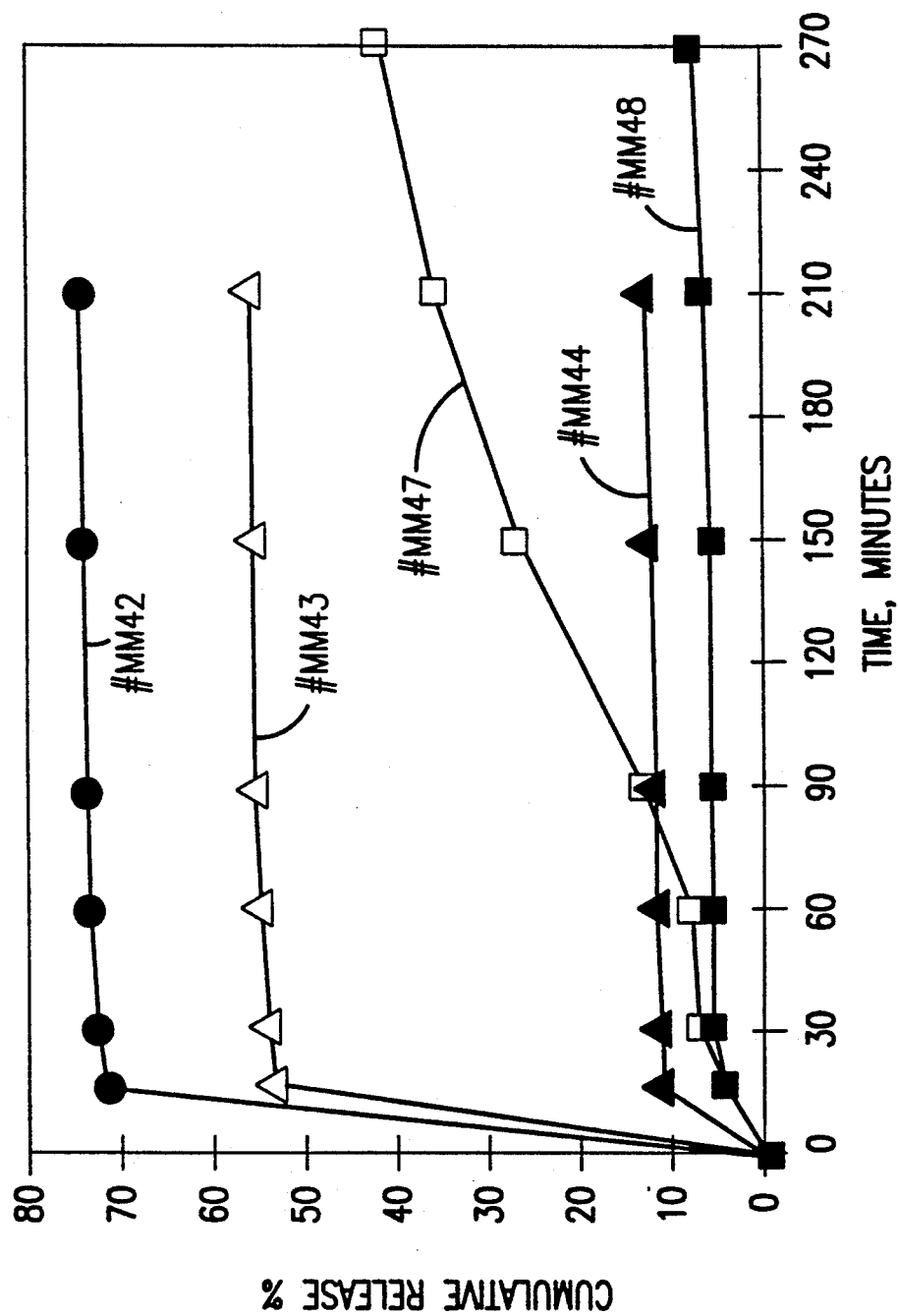
FIG. 1 shows the cumulative release percentage of CPC from the films produced by the drying of 5 varnish compositions.

One aspect of the present invention this invention relates to oral compositions that provide sustained, efficient, inexpensive, anti-plaque activity without deleterious side effects, and methods for using such compositions. The compositions of concern to the present invention are termed "varnish" compositions. Such compositions are liquids which (by polymerization, evaporation, etc.) become solidified to produce a film. In accordance with the present invention, such films have the capacity to release an antibacterial agent or a hypersensitivity agent over a substantial period of time (i.e.). Thus, such films are sustained release devices.

This invention further relates to oral compositions that provide sustained, efficient, inexpensive, antihypersensitivity activity without deleterious or undesirable side effects, and methods for using such compositions.

By "sustained-release" is meant the continuous release of an active substance at efficacious levels for a prolonged period of time, such as one hour or longer. The release of the active substance may be constant or pulsed, as long as efficacious levels of the active substance are provided to the surrounding milieu for the desired period of time.

By an "efficacious level" is meant a level or concentration of a drug or other active agent which is high enough to be effective in treating the condition the drug was designed to treat.

By "liquid varnish composition" is meant a composition which is topically applied to a surface such as a tooth, and which dries as a film adhering to that surface, in a manner which resists removal under normal conditions, such as eating or brushing the teeth.

I. The Antibacterial Agents of the Present Invention

As used herein, the term "antibacterial agent" includes both bacteriocidal and bacteriostatic agents. Such an agent is an anti-plaque agent, or an anti-caries agent, if, when provided in an effective amount to a recipient, it is capable of preventing or attenuating the accumulation of plaque or caries. A variety of bacteriocidal agents are suitable for the present invention. Preferred are the cationic nitrogen-containing antibacterial materials that are well known to the art. See, for example, the section on "Quaternary Ammonium and Related Compounds" in the article on "Antiseptics and Disinfectants" in Kirk-Othmer Encyclopedia of Chemical Technology, 2nd ed. (Vol. 2, pp. 632-5), incorporated herein by reference. Such materials have been used in oral compositions to counter plaque formation caused by bacteria in the oral cavity. Among the most common and efficacious of these antibacterial, antiplaque quaternary ammonium compounds are cetylpyridinium chloride and benzalkonium chloride. Other cationic ammonium antibacterial agents of this type are mentioned, for instance, in U.S. Pat. Nos. 2,984,639, 3,325,402, 3,431,208, 3,703,583, and 4,339,430, British Patent No. 1,319,396, and German Patent No. 2,332,383. Most preferred is cetylpyridinium chloride, which is efficacious, compatible with the other components of the oral composition, and inexpensive by virtue of being a non-prescription drug.

The compilation of the components of the aforementioned oral composition is based upon the specific properties of each of the individual components, wherein each component of the combination increases the antiplaque effectiveness of other members of the combination.

The oral composition of the invention assists in the prevention of dental caries and periodontal disease, and in the relief of symptoms resulting from existing gingival and subgingival problems, by attacking the pathogenic bacteria responsible for plaque formation and consequent cariotic and periodontal diseases.

It is also a feature of this invention that the aforementioned bacteriocidal antiplaque agent is released to the sites of carious lesions and periodontal pockets in a long-term sustained release manner so as to reduce the required frequency of use.

II. The Hypersensitivity Agents of the Present Invention

A "hypersensitivity agent" is an agent which is capable of treating tooth hypersensitivity when provided in an effective amount to a recipient in need of such treatment. A variety of anti-hypersensitivity agents are suitable for the present invention. Preferred is the use of strontium salts. Other anti-hypersensitivity agents useful in the composition of the invention include potassium, lithium or sodium nitrate, potassium bicarbonate, potassium chloride, hydroxyapatite, fluorapatite, ammonium oxalate, EDTA with fluoride, fluoride, and ammonium glycyrrhizzinate.

III. The Polymer of the Varnish of the Present Invention

The use of the above-described antibacterial and hypersensitivity agents, for dental purposes, in certain hydrophilic or acrylic polymer based sustained release compositions is disclosed in U.S. patent applications Ser. Nos. 07/189,918, abandoned, and 07/304,091, abandoned which applications are herein incorporated by reference.

The sustained release of the above-described antibacterial and hypersensitivity agents, is, in accordance with the present invention, preferably accomplished by embedding the agent in an acrylic polymer, a hydrophilic polymer, or a combination of hydrophilic and hydrophobic polymers, to form a varnish for oral administration. The use of these polymers has the additional advantage of minimizing side effects such as staining of teeth and dentures and unpleasant taste (see, for example, Friedman, M., et al., 1984 and 1985, supra).

Polymers of special interest to the present invention include hydrophilic polymers such as polymethacrylates containing more than 50% methacrylic acid monomers, relatively hydrophilic polymers such as polymethacrylics containing quaternary amine groups, and combinations of hydrophilic and hydrophobic polymers in various ratios.

The preferred polymers of the present invention are polymethacrylates such as EUDRAGIT® (Roehm Pharma GmbH, Darmstadt, Federal Republic of Germany). EUDRAGIT exists in four forms: S, L, RS and RL (*Drugs and the Pharmaceutical Sciences vol. 36*, McGinity, J. W. (ed.), Marcel Dekker, Inc., N.Y. (1989); Chafi, N. et al., *Drug. Dev. Ind. Pharm.* 15:629-648 (1989); Chang, R.-K., et al., *Drug. Dev. Ind. Pharm.* 15:361-372 (1989); Thoennes, C. J. et al., *Drug. Dev. Ind. Pharm.* 15:165-186 (1989); Silva, J. F. P. D. et al., *Folha Med.* 97:253-257 (1988); Larroche, C. et al., *Enzyme Microb. Technol.* 11:106-112 (1989); Rachmilewitz, D. et al., *Brit. Med. J.* 298:82-86 (1989); Goto, S. et al., *J. Microencapsul.* 5:343-360 (1988); which references are incorporated herein by reference).

EUDRAGIT RL and RS are water insoluble copolymers synthesized from acrylic and methacrylic acid esters with a low content of quaternary ammonium groups. These polymers form nondegradable or nondisintegrating films. If more hydrophilic polymer is added to the film, such as EUDISPERT® (Dittgen, M. et al., *Pharmazie* 41:883-884 (1987); Kristl, J. et al., *Acta Pharm. Technol.* 33:140-144 (1987), which references are incorporated herein by reference), EUDRAGIT S or EUDGRAGIT L, a different sort of film can be formed which could disintegrate.

EUDRAGIT L (or S) and EUDISPERT are anionic co-polymers based on methacrylic acid and methyl methacrylate. EUDISPERT L is soluble in buffer solutions above pH 6.0. Due to the fact that EUDISPERT is a polycarboxylic acid salt which could react with cationic drugs, it is not preferable to prepare films from varnishes containing EUDISPERT polymer alone. EUDISPERT was used successfully as an additive, however, for altering drug release from films. EUDRAGIT L, in contrast, formed nice and homogeneous films which degraded in phosphate buffer pH 6.8.

Although all of the four forms of EUDRAGIT are hydrophilic, it is harder to dissolve the RL/RS forms, than the L/S forms, in saliva. It is therefore preferable to add a plasticizer (such as, for example, polyethylene glycol, dibutyl phthalate, etc.) to the RL/RS form polymers in order to increase the rate of solubility of the R forms in saliva.

In order to increase the rate of degradation, and to increase the release of drug, it is possible to add agents such as citric acid, lysine, aspartic acid, glutamic acid, glutaric acid, etc.

The EUDRAGIT S or EUDRAGIT L polymers are highly soluble in buffer solutions. Lysine, citric acid, and divalent cations of calcium, strontium, etc., are each capable of cross-linking EUDRAGIT S or EUDRAGIT L polymers. Thus, such agents can be added to such polymers in order to decrease the rate of dissolution of the polymer.

In another embodiment of the present invention, the oral compositions may also contain additional desirable components. For example, if desired, the adhesiveness of the oral composition may be improved by the incorporation within said composition of gums such as gum mastic in a formulation providing from 1-20% by weight of the gum mastic. Other suitable mastics are disclosed in U.S. Pat. No. 4,315,779 to Heyd, D., et al., and U.S. Pat. No. 4,374,844 to Wahmi, H. V. R., et al.

Likewise, the compositions may contain demulcents/humectants (i.e., plasticizers) such as polyethylene glycol 400-to-4000, glycerol, sorbitol, or mineral oil in concentrations of about 1% by weight. Other humectants, detergents, or surface-active agents will be known to those skilled in the formulation of oral compositions. Polyethylene glycols or dibutyl phthalate are the preferred optional plasticizers of the invention. Such agents play a role in enhancing the rate of degradation of the film and improving its adherence.

For application to buccal and lingual surfaces of teeth, a solution of the bacteriocidal agent or the hypersensitivity agent and the polymer may be applied by spray, soft brush, etc. Solvent may be evaporated by a gentle stream of warm air, or by other means.

For application to orthodontic appliances, a total of about 70 mg of bacteriocidal agent, dissolved in polymer may be applied per appliance with a soft brush or spray, and residual solvent removed with a gentle stream of warm air.

Those skilled in the art of plaque prevention will, without undue experimentation, be able to produce ranges of concentrations of other appropriate bacteriocidal agents and sustained release polymers.

In yet another embodiment, the composition may contain an oxygenating agent. Such an agent will be present in an amount capable an anti-caries, anti-plaque or antiseptic-like effect. Examples of suitable oxygenating agents include urea peroxide, hydrogen peroxide (Cameron, J. A. et al., *Austral. Dent. J.* 29:80-85 (1984); Firestone, A. R. et al., *Caries Res.* 16:112-117 (1982); Futaki, S. et al., *Shikwa Gakuho* 80:487-495 (1980)), carbamide peroxide (Ullmann, E. et al., *Somatol. DDR* 33:334-341 (1983)), peroxyborate monohydrate (Addy, M. et al., *J. Clin. Immunol.* 5:272-277 (1978); Dill, H. et al., *Int. J. Clin. Pharmacol. Biopharm.* 15:17-18 (1977)), and peroxydiphosphate (Afflitto, J. et al., *J. Dent. Res.* 67 (Spec. Iss. March):401 (1988); Coleman, E. J. et al. *J. Dent. Res.* 67 (Spec. Iss. March):296 (1988); Nabi. N. et al., *J. Dent. Res.* 67 (Spec. Iss. March):151 (1988)).

Having now generally described the invention, the same will become better understood by reference to certain specific examples which are included herein for purposes of illustration only and are not intended to be limiting unless otherwise specified.

EXAMPLE 1

Since toothbrushing generally proves to be sufficient in preventing plaque, the use of chemicals which reduce plaque and could be delivered in forms likely to be widely accepted by the general public have been assiduously sought by dental scientists. Many quaternary ammonium salts in the form of mouthwashes, dentifrice, solutions and gels have proven successful in preventing periodontal diseases. Among them, chlorhexidine and ceytlpyridium chloride (CPC) are the most effective against plaque.

Sustained release drug treatment is expected to be efficacious in local and prolonged action rather than the conventional antibacterial therapy (mouthrinse and dentifrice). Thus, a CPC varnish solution which can be spread on the teeth to form a drug-containing film is desirable. The drug is expected to be released into the mouth cavity and into plaque substance which accumulates on teeth. The release should be terminated after a night's sleep (average: 5-6 hours), while at the same time, the film degrades.

In an attempt to assess the in vitro release of CPC from varnish films composed of acrylic polymers, a broad series of experiments were performed in which different polymers and plasticizers and several additives were formulated and tested.

1. Varnish Preparation—General Description

The formulations were all prepared by the same general procedure, described as follows: the polymer (EUDRAGIT ®, Roehm Pharma Gmbh, Darmstadt, W. Germany), polyethylene glycol (PEG), and the CPC were dissolved in ethanol. After complete dissolution of these ingredients, additional components in aqueous solution were added, while continuously stirring. The ratio of film components to solvents (water/alcohol) was 1:3.

2. In-vitro evaluation

Varnish solutions containing the requisite weights of CPC and polymer were poured on Teflon plates. The films were generated after allowing the solvent to evaporate for 12-15 hours at room temperature. The films (containing 1-5% water) were cut to rectangular forms of 1 × 1 cm in an area and accurately weighed. The films were then placed in vials containing 5 ml phosphate buffer (0.02M, pH 6.8) previously warmed to 37° C. and incubated for 6 hours. Samples were taken at time intervals of 5, 15, 30, 60, 90, 210, 270, 330, and 360 minutes. The concentration of CPC released was determined by UV spectrophotometer (UVIKON 930, Kontron Instruments) at 254 nm against standard calibration curve.

In these experiments, EUDISPERT mv or EUDRAGIT L was added to the formulations containing CPC and EUDRAGIT RL. EUDISPERT mv and EUDRAGIT L are relatively water-soluble polymers. Table I shows the weight percent of components in films prepared from 5 varnish compositions (i.e. MM42, MM43, MM44, MM47, and MM48). The liquid compositions were dried, and the cumulative percentage of released CPC was determined. FIG. 1 shows the cumulative release percentage of CPC from the films produced by the drying of the 5 varnish compositions.

TABLE I

| Exp. No. | MM42 | MM43 | MM44 | MM47 | MM48 |
|---|---|---|---|---|---|
| Weight percent of components in film formulations | | | | | |
| CPC | 30 | 30 | 30 | 30 | 30 |
| EUDRAGIT RL | 35 | 32.5 | 30 | 40 | 55 |
| PEG 400 | 25 | 25 | 25 | — | — |
| EUDRAGIT L | — | — | — | 30 | — |
| EUDISPERT mv | 10 | 12.5 | 15 | — | 15 |

EXAMPLE 2

Figure 2:
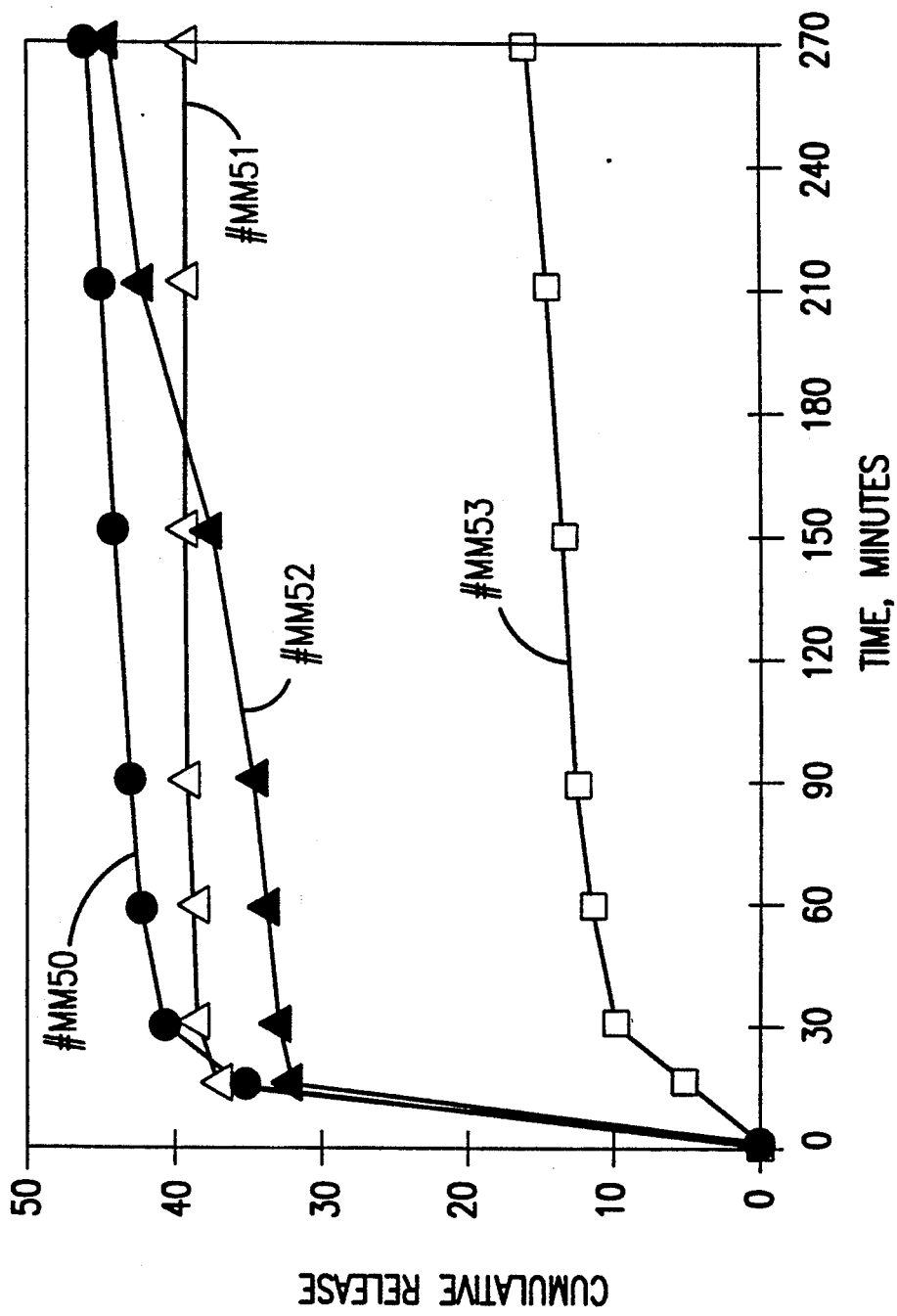
FIG. 2 shows the cumulative release percentage of CPC from the films produced by the drying of 4 varnish compositions.

In these experiments EUDISPERT mv or EUDRAGIT L were added to formulations containing a combination of 50:50 EUDRAGIT RL/EUDRAGIT RS either with PEG 400 or without it. Table II shows the weight percent of components in films prepared from 4 varnish compositions (i.e. MM50, MM51, MM52, and MM53). The liquid compositions were dried, and the cumulative percentage of released CPC was determined. FIG. 2 shows the cumulative release percentage of CPC from the films produced by the drying of the 4 varnish compositions.

TABLE II

| Exp. No. | MM50 | MM51 | MM52 | MM53 |
|---|---|---|---|---|
| Weight percent of components in film formulations | | | | |
| CPC | 30 | 30 | 30 | 30 |
| EUDRAGIT RL | 15 | 25 | 20 | 30 |
| EUDRAGIT RS | 15 | 25 | 20 | 30 |
| PEG 400 | 10 | 10 | 20 | 30 |
| EUDRAGIT L | 30 | — | 30 | — |
| EUDISPERT mv | — | 10 | — | 10 |

EXAMPLE 3

Figure 3:
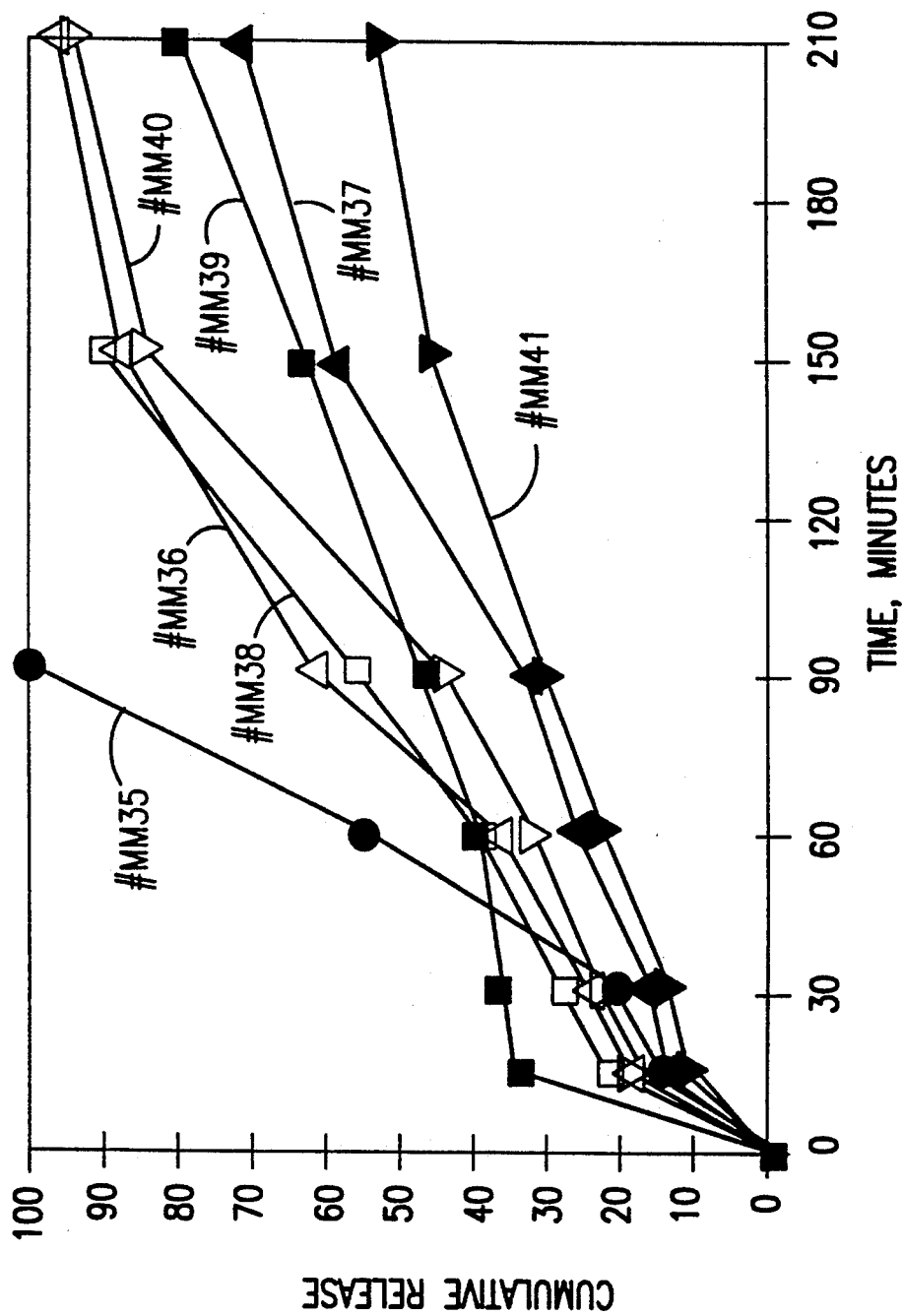
FIG. 3 shows the cumulative release percentage of CPC from the films produced by the drying of 7 varnish compositions.

This example involved various Eduispert mv concentrations in formulations containing CPC, EUDRAGIT L and PEG 400. Table III shows the weight percent of components in films prepared from 7 varnish compositions (i.e. MM35, MM36, MM37, MM38, MM39, MM40 and MM41). The liquid compositions were dried, and the cumulative percentage of released CPC was determined. FIG. 3 shows the cumulative release percentage of CPC from the films produced by the drying of the 7 varnish compositions.

TABLE III

| Exp. No. | MM35 | MM36 | MM37 | MM38 | MM39 | MM40 | MM41 |
|---|---|---|---|---|---|---|---|
| CPC | 30 | 30 | 30 | 30 | 30 | 30 | 30 |
| EUDRAGIT L | 45 | 42.5 | 40 | 37.5 | 35 | 32.5 | 30 |
| PEG 400 | 25 | 25 | 25 | 25 | 25 | 25 | 25 |

TABLE III-continued

| Exp. No. | MM35 | MM36 | MM37 | MM38 | MM39 | MM40 | MM41 |
| --- | --- | --- | --- | --- | --- | --- | --- |
| EUDISPERT mv | — | 2.5 | 5 | 7.5 | 10 | 12.5 | 15 |

EXAMPLE 4

Figure 4:
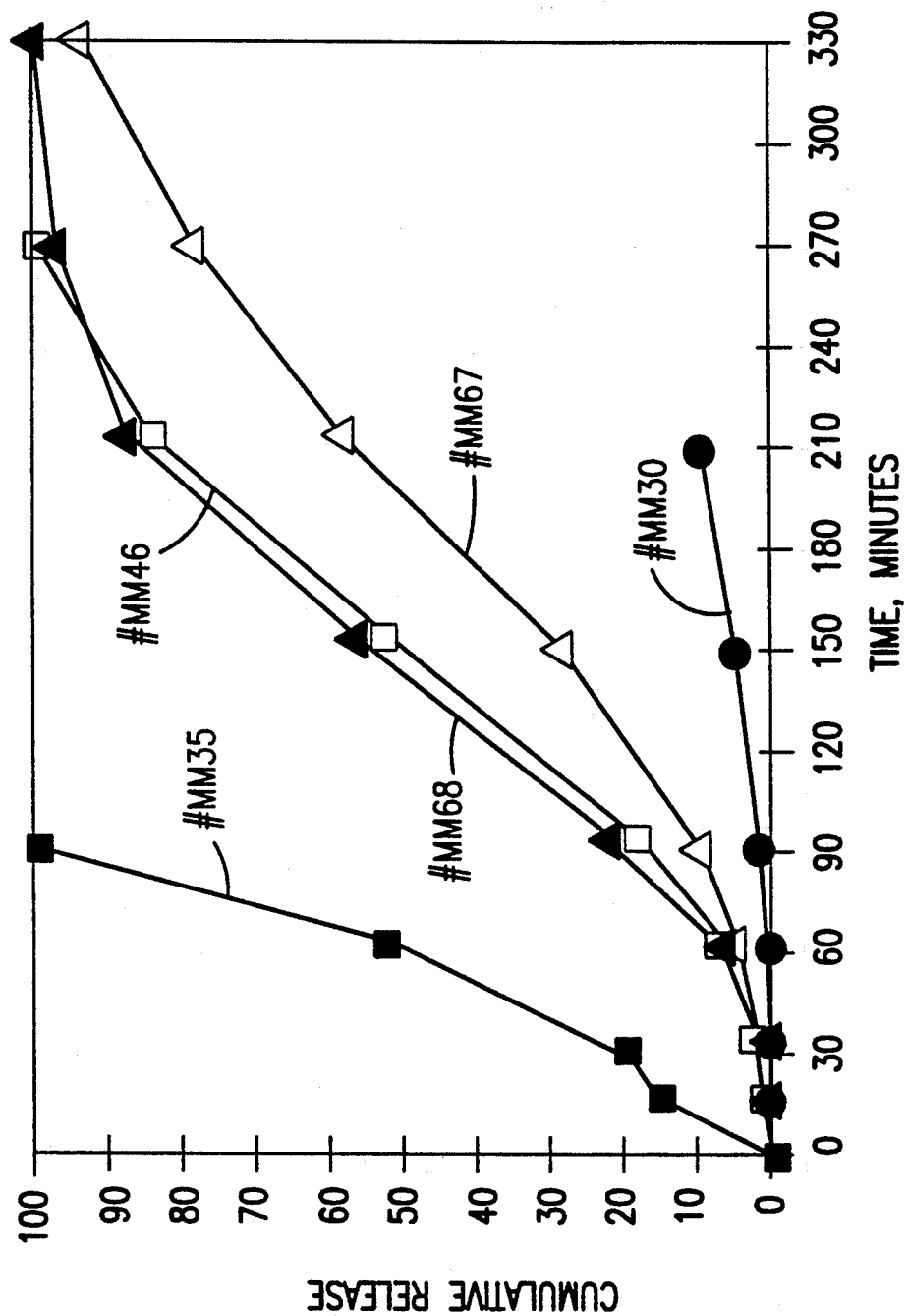
FIG. 4 shows the cumulative release percentage of CPC from the films produced by the drying of 5 varnish compositions.

CPC and EUDRAGIT L preparations were made containing various PEG 400 concentrations. Table IV shows the weight percent of components in films prepared from 5 varnish compositions (i.e. MM30, MM67, MM68, MM46 and MM35). The liquid compositions were dried, and the cumulative percentage of released CPC was determined. FIG. 4 shows the cumulative release percentage of CPC from the films produced by the drying of the 5 varnish compositions.

TABLE IV

| Exp. No. | MM30 | MM67 | MM68 | MM46 | MM35 |
| --- | --- | --- | --- | --- | --- |
| CPC | 30 | 30 | 30 | 30 | 30 |
| EUDRAGIT L | 70 | 65 | 60 | 55 | 45 |
| PEG 400 | — | 5 | 10 | 15 | 25 |

EXAMPLE 5

Figure 5:
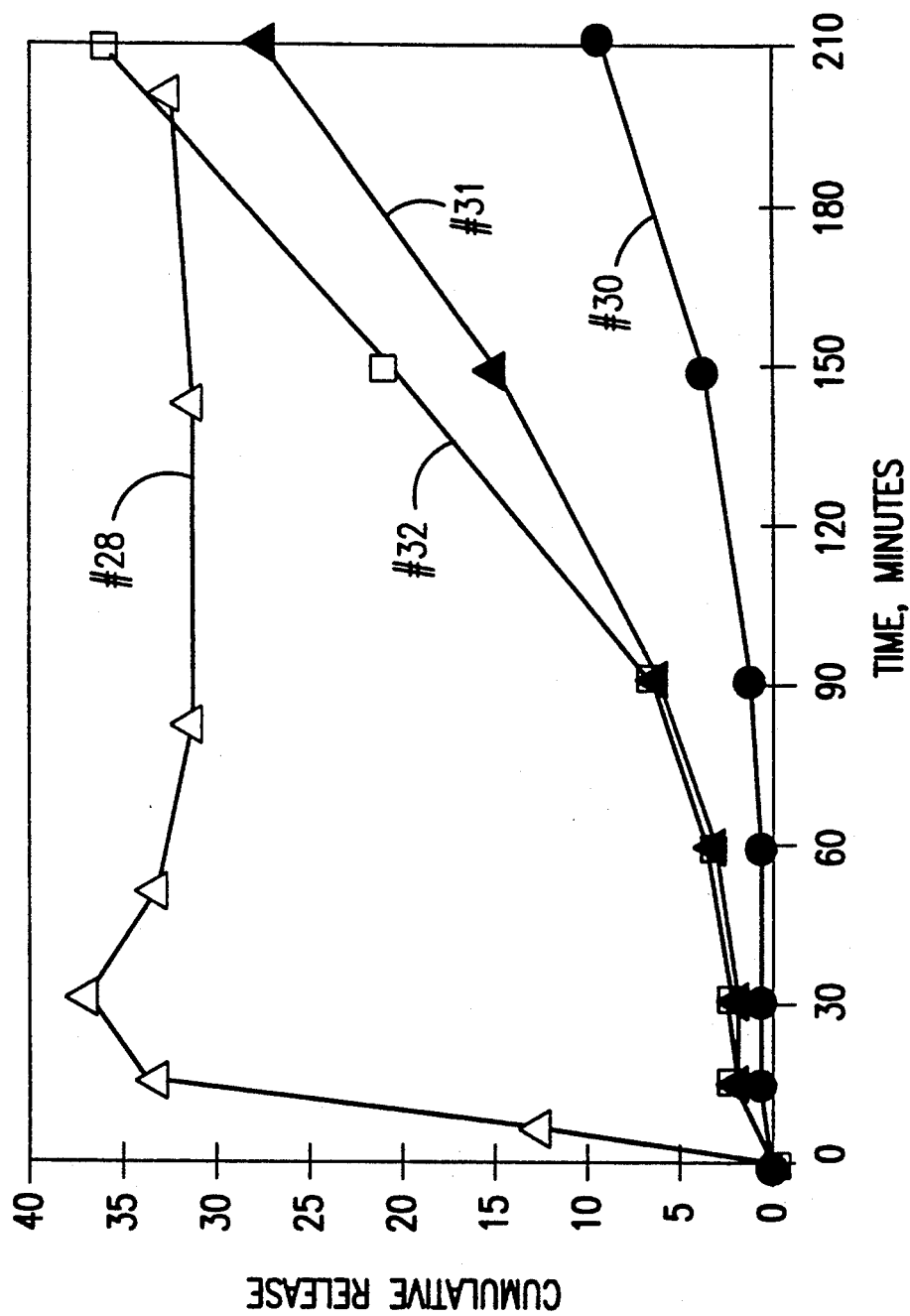
FIG. 5 shows the cumulative release percentage of CPC from the films produced by the drying of 4 varnish compositions.

These experiments included an addition of various concentrations of citric acid as release enhancers. Table V shows the weight percent of components in films prepared from 4 varnish compositions (i.e. MM30, MM28, MM31, and MM32). The liquid compositions were dried, and the cumulative percentage of released CPC was determined. FIG. 5 shows the cumulative release percentage of CPC from the films produced by the drying of the 4 varnish compositions.

TABLE V

| Exp. No. | MM30 | MM28 | MM31 | MM32 |
| --- | --- | --- | --- | --- |
| CPC | 30 | 30 | 30 | 30 |
| EUDRAGIT L | 70 | 60 | 65 | 67.5 |
| CITRIC ACID | — | 10 | 5 | 2.5 |

EXAMPLE 6

Figure 6:
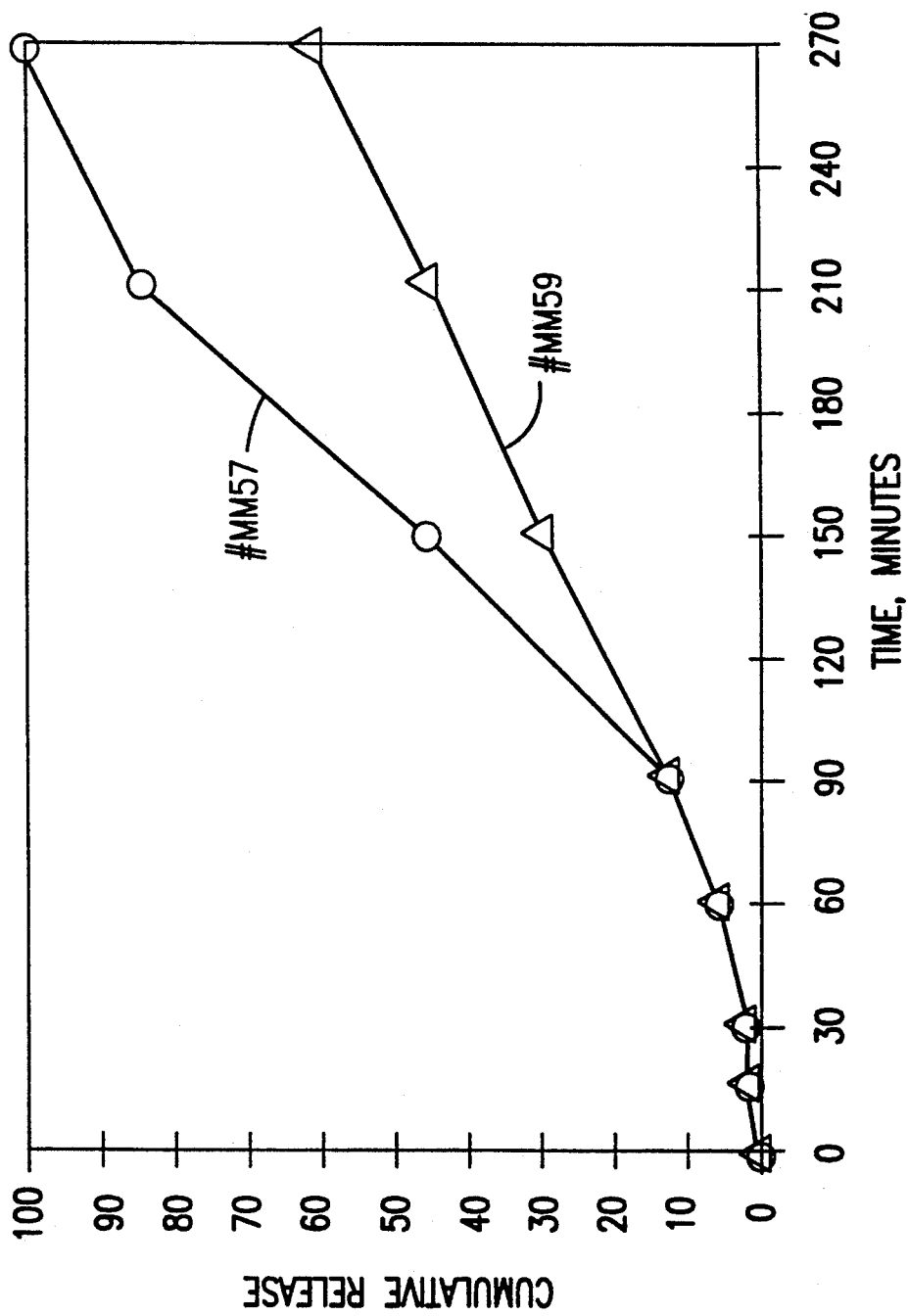
FIG. 6 shows the cumulative release percentage of CPC from the films produced by the drying of 4 varnish compositions.

Two formulations containing 0.3% lysine (in film), EUDRAGIT L, and CPC were prepared. Only one was prepared with PEG 400. The ability of these preparations to mediate drug release was determined. Table VI shows the weight percent of components in films prepared from 2 varnish compositions (i.e. MM57 and MM59). The liquid compositions were dried, and the cumulative percentage of released CPC was determined. FIG. 6 shows the cumulative release percentage of CPC from the films produced by the drying of the 4 varnish compositions.

TABLE VI

| Exp. No. | MM57 | MM59 |
| --- | --- | --- |
| CPC | 30 | 30 |
| EUDRAGIT L-100 | 54.7 | 69.7 |
| LYSINE HCl | 0.3 | 0.3 |
| PEG 400 | 15 | — |

EXAMPLE 7

Figure 7:
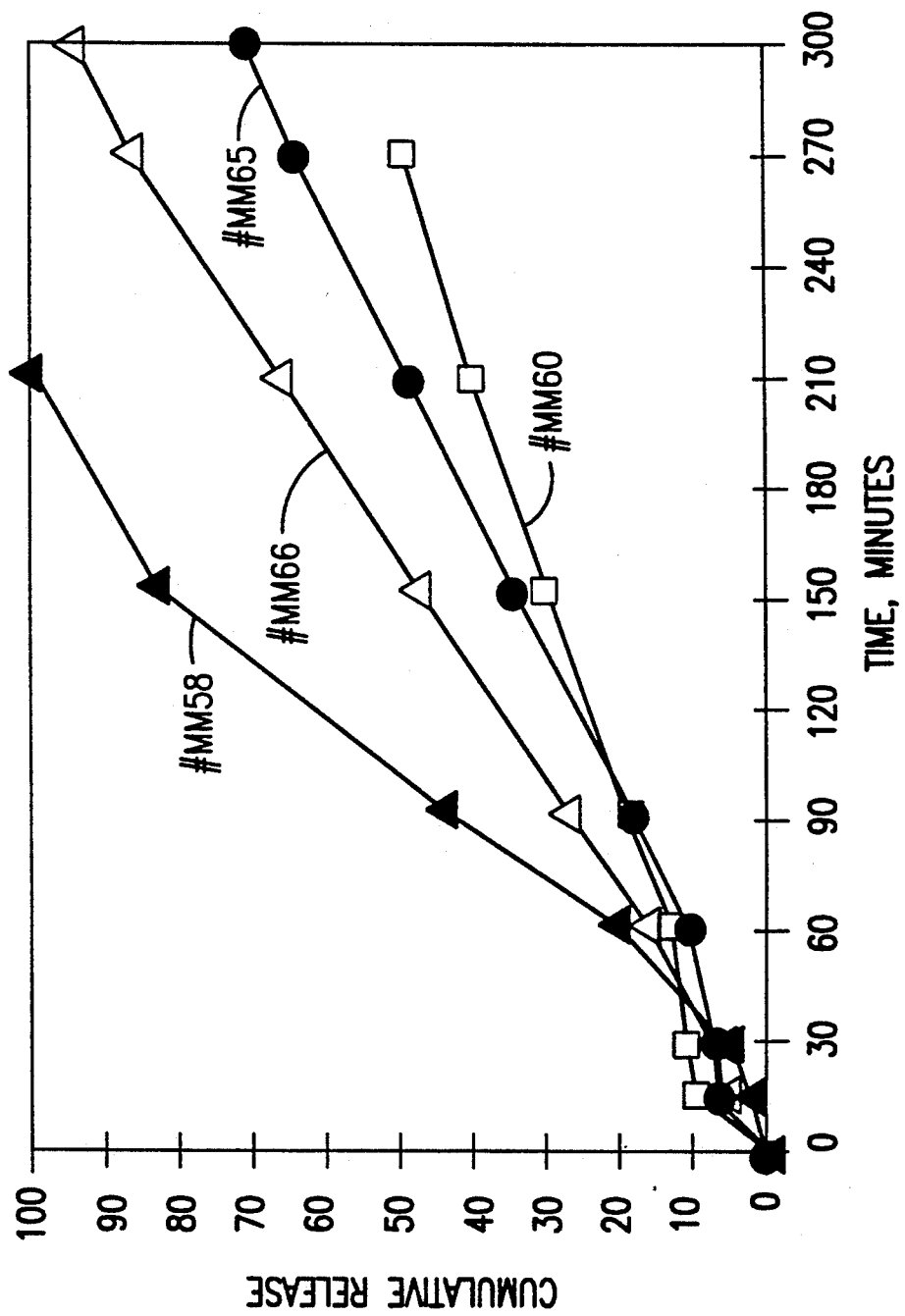
FIG. 7 shows the cumulative release percentage of CPC from the films produced by the drying of 4 varnish compositions.

These formulations were prepared with 0.5% lysine (in film) EUDRAGIT L, CPC and various concentrations of PEG 400. Table VII shows the weight percent of components in films prepared from 4 varnish compositions (i.e. MM60, MM65, MM66, and MM58). The liquid compositions were dried, and the cumulative percentage of released CPC was determined. FIG. 7 shows the cumulative release percentage of CPC from the films produced by the drying of the 4 varnish compositions.

TABLE VII

| Exp. No. | MM60 | MM65 | MM66 | MM58 |
| --- | --- | --- | --- | --- |
| CPC | 30 | 30 | 30 | 30 |
| EUDRAGIT L | 69.5 | 64.5 | 59.5 | 54.5 |
| LYSINE HCl | 0.5 | 0.5 | 0.5 | 0.5 |
| PEG 400 | — | 5 | 10 | 15 |

EXAMPLE 8

Figure 8:
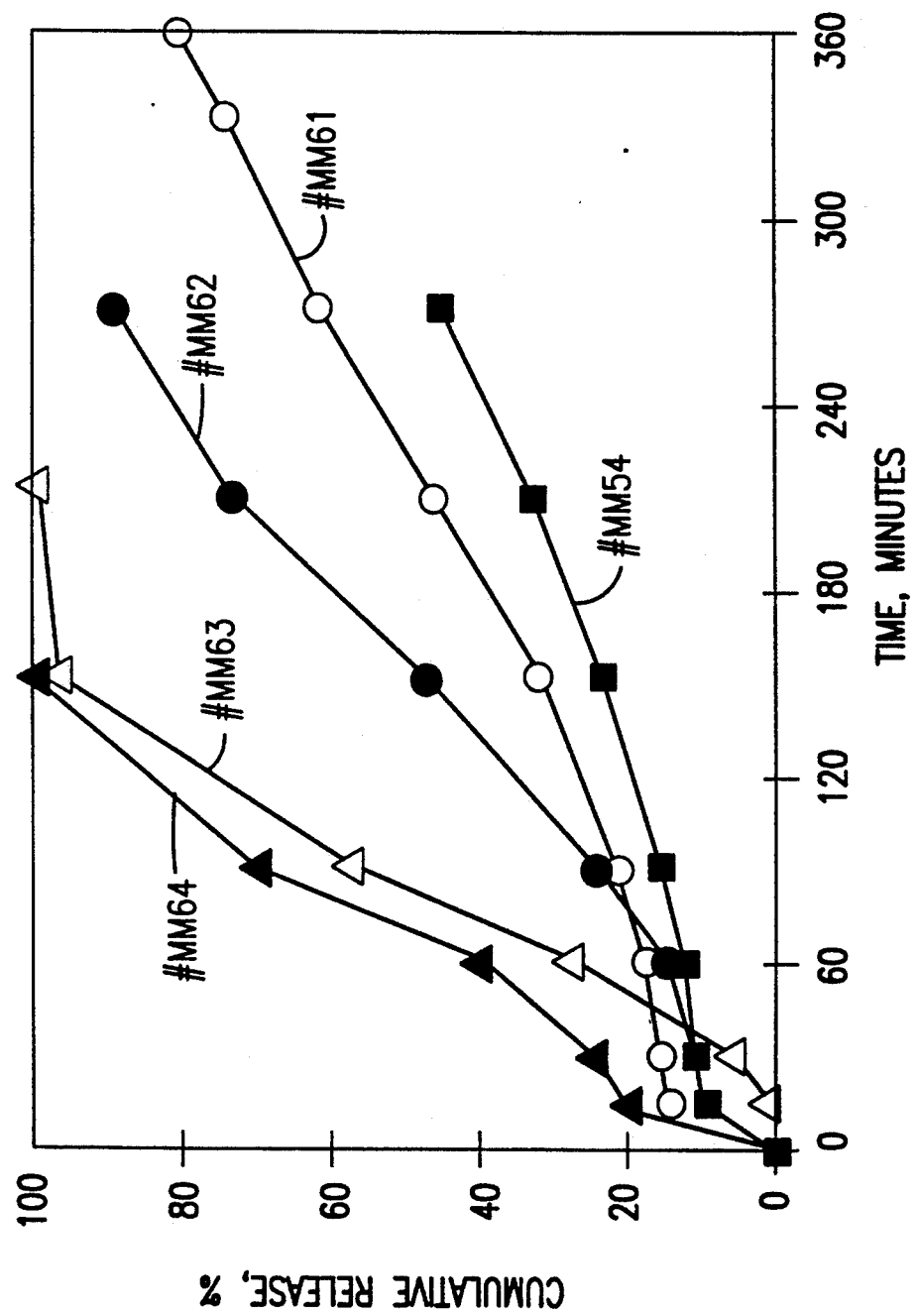
FIG. 8 shows the cumulative release percentage of CPC from the films produced by the drying of 5 varnish compositions.

Formulations were prepared with 1% of lysine (in film), EUDRAGIT L, CPC and various concentrations of PEG 400. Table VIII shows the weight percent of components in films prepared from 5 varnish compositions (i.e. MM54, MM61, MM62, MM63 and MM64). The liquid compositions were dried, and the cumulative percentage of released CPC was determined. FIG. 8 shows the cumulative release percentage of CPC from the films produced by the drying of the 5 varnish compositions.

TABLE VIII

| Exp. No. | MM54 | MM61 | MM62 | MM63 | MM64 |
| --- | --- | --- | --- | --- | --- |
| CPC | 30 | 30 | 30 | 30 | 30 |
| EUDRAGIT L | 69 | 64 | 59 | 54 | 49 |
| LYSINE HCl | 1 | 1 | 1 | 1 | 1 |
| PEG 400 | — | 5 | 10 | 15 | 20 |

EXAMPLE 9

Figure 9:
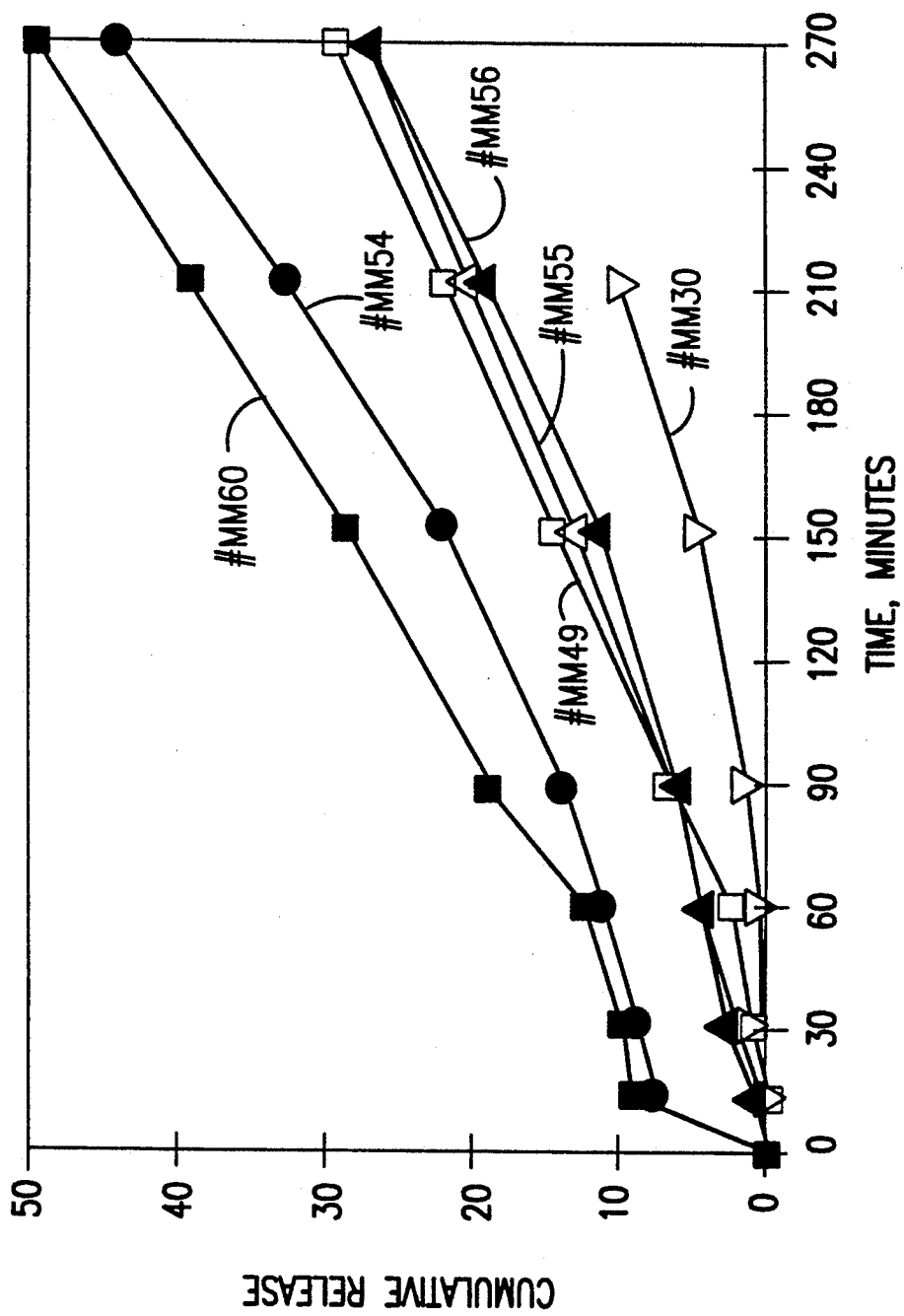
FIG. 9 shows the cumulative release percentage of CPC from the films produced by the drying of 6 varnish compositions.

In these experiments, no PEG was included. They were prepared with CPC, EUDRAGIT L and various concentrations of lysine. Table IX shows the weight percent of components in films prepared from 6 varnish compositions (i.e. MM30, MM60, MM54, MM55, MM56 and MM49). The liquid compositions were dried, and the cumulative percentage of released CPC was determined. FIG. 9 shows the cumulative release percentage of CPC from the films produced by the drying of the 6 varnish compositions.

TABLE IX

| Exp. No. | MM30 | MM60 | MM54 | MM55 | MM56 | MM49 |
| --- | --- | --- | --- | --- | --- | --- |
| CPC | 30 | 30 | 30 | 30 | 30 | 30 |
| EUDRAGIT L | 70 | 69.5 | 69 | 68 | 67 | 65 |
| LYSINE HCl | — | 0.5 | 1 | 2 | 3 | 5 |

EXAMPLE 10

Figure 10:
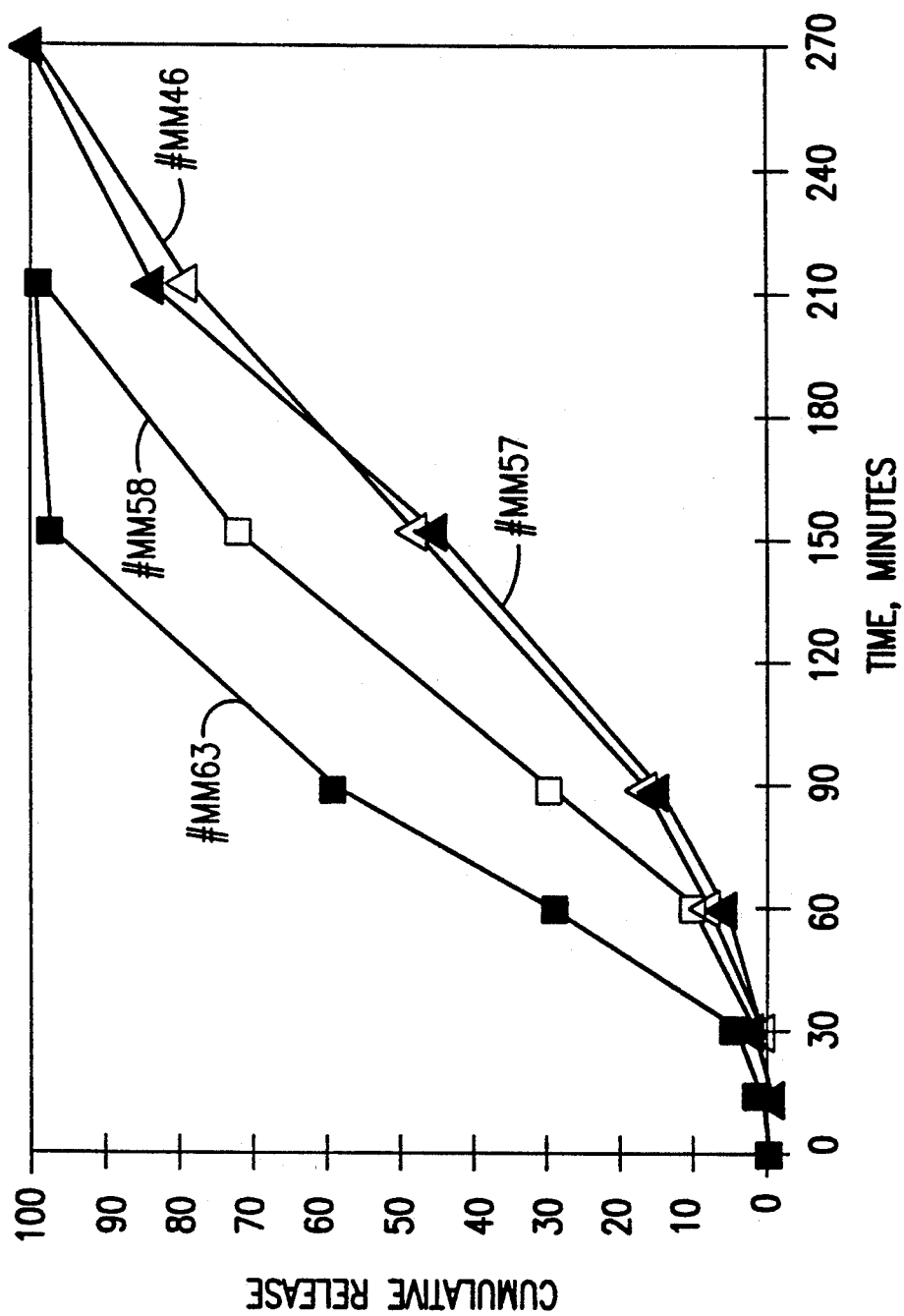
FIG. 10 shows the cumulative release percentage of CPC from the films produced by the drying of 4 varnish compositions.

Formulations were prepared containing 15% PEG 400 (in film). They were prepared with CPC, EUDRAGIT L, PEG 400 and various concentrations of lysine. Table X shows the weight percent of components in films prepared from 4 varnish compositions (i.e. MM46, MM57, MM58, and MM63). The liquid compositions were dried, and the cumulative percentage of released CPC was determined. FIG. 10 shows the cumulative release percentage of CPC from the films produced by the drying of the 4 varnish compositions.

TABLE X

| Exp. No. | MM46 | MM57 | MM58 | MM63 |
|---|---|---|---|---|
| CPC | 30 | 30 | 30 | 30 |
| EUDRAGIT L | 55 | 54.7 | 54.5 | 54 |
| PEG 400 | 15 | 15 | 15 | 15 |
| LYSINE HCl | — | 0.3 | 0.5 | 1 |

EXAMPLE 11

Figure 11:
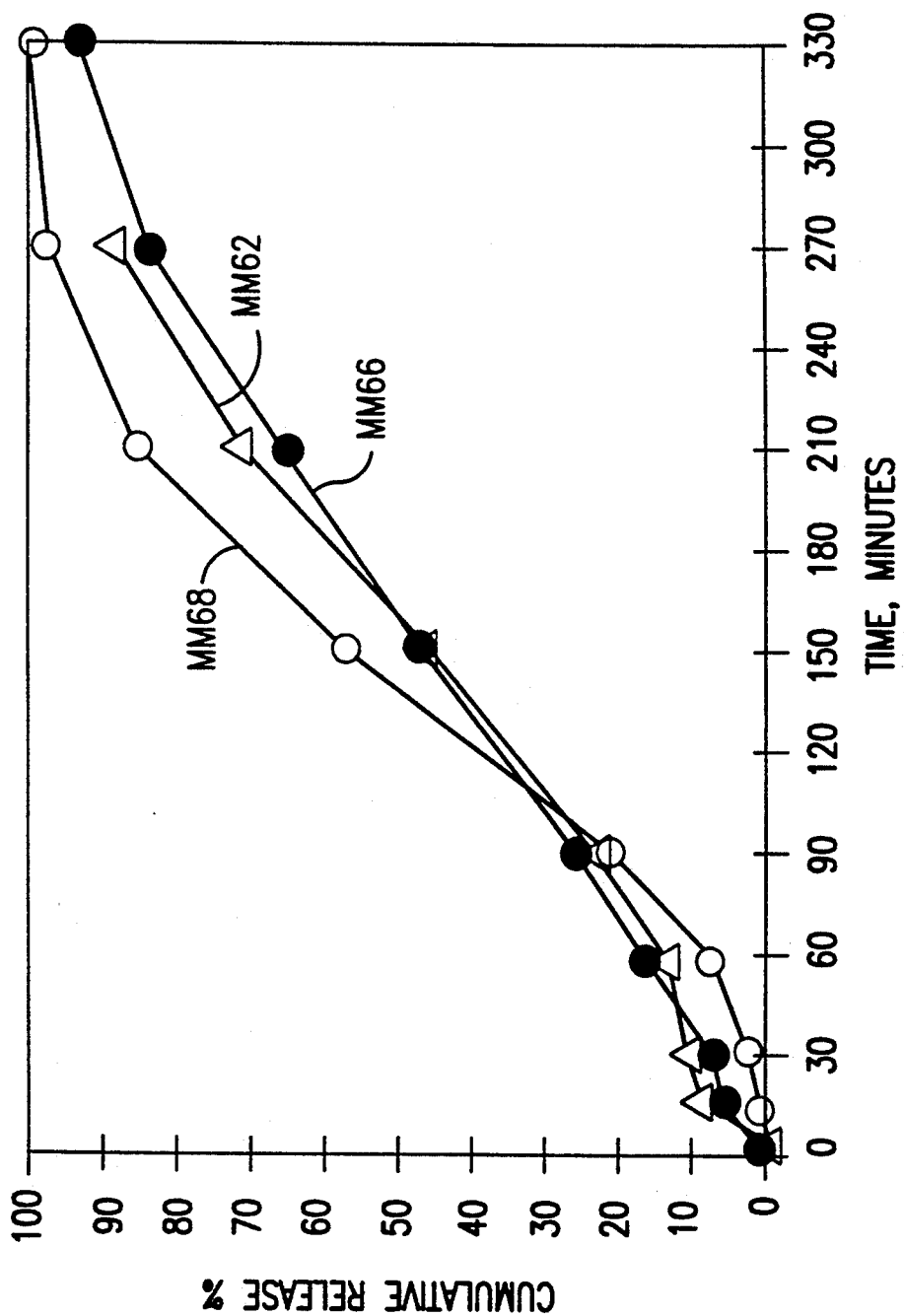
FIG. 11 shows the cumulative release percentage of CPC from the films produced by the drying of 3 varnish compositions.

Formulations were prepared containing 10% PEG 400 (in film). They were prepared wit CPC, EUDRAGIT L, PEG 400 and various concentrations of lysine. Table XI shows the weight percent of components in films prepared from 3 varnish compositions (i.e. MM68, MM66, and MM62). The liquid compositions were dried, and the cumulative percentage of released CPC was determined. FIG. 11 shows the cumulative release percentage of CPC from the films produced by the drying of the 3 varnish compositions.

TABLE XI

| Exp. No. | MM68 | MM66 | MM62 |
|---|---|---|---|
| CPC | 30 | 30 | 30 |
| EUDRAGIT L | 60 | 59.5 | 59 |
| PEG 400 | 10 | 10 | 10 |
| LYSINE HCl | — | 0.5 | 1 |

EXAMPLE 12

A Summary of formulations containing various amounts of PEG 400 and lysine with their degradation times in buffer solution (0.02M, pH 6.8) was determined. Table XII shows the affect on degradation caused by altering the percent PEG 400 and % lysine components in films prepared from 14 varnish compositions. The liquid compositions were dried, and the time of disappearance of the film was determined.

TABLE XII

| | Exp. No. | % PEG | % lysine | Time of disappearance |
|---|---|---|---|---|
| A. | MM35 | 25 | — | 90 |
| | MM46 | 15 | — | 270 |
| | MM66 | 10 | — | 300 |
| | MM67 | 5 | — | 330 |
| | MM30 | — | — | >360 |
| B. | MM64 | 20 | 1 | 150 |
| | MM63 | 15 | 1 | 210 |
| | MM62 | 10 | 1 | 330 |
| | MM61 | 5 | 1 | >360 |
| | MM54 | — | 1 | >360 |
| C. | MM58 | 15 | 0.5 | 210 |
| | MM66 | 10 | 0.5 | 330 |
| | MM65 | 5 | 0.5 | >360 |
| | MM60 | — | 0.5 | >360 |

EXAMPLE 13

Sustained release of CPC from film matrices was achieved with an array of formulations possessing a broad range of kinetic profiles (FIGS. 1-10). Films which were prepared with EUDRAGIT RL/RS were not homogeneously formed unless EUDISPERT mv was added. Moreover, by incorporating EUDISPERT polymer in the matrices, a partially degradable film could be achieved, however, these films released the drug within 15-20 minutes and a plateau was then observed.

FIG. 1 shows a drastic decrease in the total amount of drug released (after the short burst) when EUDISPERT concentrations increase by small increments (10%, 12.5%, and 15%). This exhibits a possible interaction between drug, EUDISPERT and EUDRAGIT RL polymers, or a presence of some sort of cross-linking which can form between the polymeric chains, resulting in drug trapping in the matrix. The use of EUDRAGIT L, which contains lower molar concentration of carboxylic acid groups than EUDISPERT, thoroughly changes the release profile of CPC (see FIGS. 1 and 2).

By adding PEG 400 to the formulations (MM50 and MM51), the difference in the release patterns were significantly diminished (FIG. 2). Films which were prepared with EUDRAGIT L were quite different in their features. FIG. 4 shows the release of CPC from EUDRAGIT L films containing elevating concentrations of PEG. In addition to the influence of PEG on the release kinetics, the disintegration time was also dependant upon its concentration as can be seen in Table XII-A. In comparison, citric acid changes the release kinetics (FIG. 5), but does not affect the solubility or the degradability of the films.

FIGS. 6-10 demonstrate the contribution of lysine hydrochloride to the release of CPC from EUDRAGIT L films. When no PEG was used in the formulations (FIG. 9), the addition of 0.5 to 5% of lysine significantly increased the rate of CPC release, but no substantive difference between the various lysine concentrations was observed. When 15% PEG 400 was added to the formulations (see FIG. 10), the rate of CPC release was also increased with the rise of lysine content from 0.5% and above. No significant change in the release kinetics was noticed in a formulation containing 0.3 of lysine. In contrast to this phenomenon, the addition of 10% PEG or less did not increase the release rate but significantly changed the kinetic profile of CPC release. As can be seen in FIG. 11, the addition of 0.5% and 1% lysine smoothed the curve and formed a constant rate of release.

The disintegration rate of CPC-EUDRAGIT L films is also affected by lysine, as is indicated in Table XII. The addition of 0.5% or 1% lysine hydrochloride to the film increased the time taken for the film to disappear by approximately 30 minutes (300 to 330 minutes and 330 to over 360 minutes). There was one exception in a formulation which contained 15% PEG, where a decrease in time was observed (270 to 210 minutes). This exception might correspond to the abovementioned phenomenon of different release kinetics between formulations containing 15% PEG and various lysine concentrations and formulations with 10% PEG and less. It is postulated that two ion-exchange mechanisms of lysine action exist in order to explain the different release patterns: 1. a delay in the polymer solubilization by cross-linking interaction, and 2. a competition of lysine with the quaternary ammonium drug on the polymer's active sites.

For anti-plaque compositions, EUDRAGIT L and RL are the preferred polymers. EUDRAGIT L is the most preferred polymer for an anti-plaque composition. EUDRAGIT L was found appropriate for the preferred mode of application. It forms a homogeneous film which can disintegrate in a few hours, releasing CPC in a sustained manner. The use of PEG, citric acid, and lysine hydrochloride aid in controlling the release of the drug. PEG, and probably citric acid as well, acts as a plasticizer within the polymeric matrix. These agents act to reduce crystallinity and increasing the accessibility to water diffusion. Citric acid, which contains three carboxylic acid salts, can act also as a drug carrier by interact with the CPC's quaternary ammonium group. This interaction, which results in a soluble complex, actually competes with a similar interaction involving the polymer and the drug. The latter interaction, however, does not result in a soluble complex and it actually causes a delay in the drug release.

Lysine, in contrast, has the ability to form cross-linking bonds between the polymer backbone chains and delay the release by reducing the polymer's permeability. In fact we found the opposite, when the release rate increased with elevation of lysine concentrations (see FIGS. 9, 10). This suggests that the cross-linking mechanism is not as dominant as another mechanism of action involving interference of drug-polymer interaction by competing on the polymer's active sites. Nevertheless, the cross-linking mechanism is postulated to occur when relatively low concentrations of PEG (10% and less) are used, forming an appropriate space for the cross interaction. As has already been noted above, the delay in the disappearance of the films which contain 10% or 5% PEG may indicate cross-linking rather than a competition mechanism.

The preferred anti-plaque composition of the present invention is formulation MM66 (FIG. 7, Table VII). This preparation contains 30% CPC, 0.5% lysine hydrochloride, 10% PEG, and EUDRAGIT L in the dried film.

There are two advantages in using this varnish preparation:

1. It releases the drug at a constant rate and in a prolonged manner,
2. It degrades or disintegrates completely (in buffer solutions) after 5.5 hours, which corresponds to overnight application.

EXAMPLE 14

Hypersensitivity of the teeth to heat, cold, sweet food or mechanical stimulation is caused by decay of the enamel or gum recession. Exposure of the dentin results in increased movement of calcium in the ion channels, which in turn causes painful stimulation of the nerve endings.

Strontium chloride has been shown to be effective in the treatment of hypersensitive teeth. It is believed to act either by entering the calcium channels and displacing calcium at the nerve endings, or by blocking the channels at the dentin surface by deposition as insoluble salts. Sensodyne toothpaste has strontium chloride as the active ingredient. Its effectiveness is limited, however, by its very short contact time, the toothpaste being washed away after a minute or two.

To overcome this limitation, a sustained-release formulation has been developed for strontium chloride by incorporating it into a biodegradable acrylic polymer. The polymer, dissolved in aqueous alcohol, is preferably "painted" on the teeth (as by soft brush, spray, etc.) to form a quickly drying film or varnish. Preferably the film will release its strontium steadily over a few hours and will itself be slowly degraded overnight. The patient will thus be able to apply the film in the evening before going to sleep and by morning it will have disappeared.

Formulation of Films

Formulations were prepared in 70% alcohol by the dissolution of EUDRAGIT L and PEG 400 (where applicable) in alcohol followed by the slow addition of aqueous solutions of strontium chloride and other salts (as applicable) to the stirred mixture. 70% alcohol was chosen as the best balance between the conflicting requirements of a film that is quick-drying but does not cause undue pain upon oral application. The ratio of total film components to total solvents in the formulations was in the range of 1:3 to 1:4 (w/v), an alcoholic polymer solution of the highest workable viscosity (c.a. 0.33 g/ml) being used every time. High concentration is a necessary requirement for a quick-drying film that can be spread or painted on the teeth, but if too viscous, the components cannot be mixed in well. Formulations containing trisodium citrate were white suspensions and those without this salt were opaque solutions.

Films were prepared by spreading each formulation over a 6.5 cm diameter teflon dish and allowing to dry overnight at room temperature. The use of a weight of formulation calculated to produce approximately 0.5 g of dry film resulted in films with a mean thickness of 194$\mu$ (standard deviation 34$\mu$).

In Vitro Release

The release of strontium from films in the mouth was stimulated in vitro. A 1.5-cm square (34–44 mg) was cut and placed in 3 ml of pH 6.8 phosphate buffer (0.04M) in a thermostatically controlled water bath at 37° C. with gentle shaking. At suitable intervals until the film had totally dissolved, the film was transferred to a fresh vial containing another 3 ml of buffer. This crudely simulated the continuous renewal of saliva in the mouth and also enabled the amount of strontium released at each time interval to be measured. The film was also weighed at hourly intervals to obtain an indication of its disintegration profile. More frequent weighings were precluded by the need to dry the film in air for at least 5 minutes before weighing.

Release of strontium and disintegration of the film are expected to be slower in vivo than in this model because of the very limited movement of saliva in the mouth during sleep. We therefore aimed for a film that would release strontium steadily over 1–2 hours and disintegrate in 2–4 hours under these experimental conditions.

Analysis for Strontium

The samples of buffer from the release experiments were analyzed for strontium content by atomic absorption with an air-acetylene flame and detection of the 460.7 nm line. Standard solutions of strontium chloride in the buffer were used to construct a calibration curve, which was found to be linear in the range of 0.5–8 $\mu$g/ml of strontium, and the samples were further diluted in the release buffer accordingly. From the weights of wet formulation on the plate, dry film, and film square, the weight of strontium in the film square could be calculated, and thus the concentrations of strontium in the samples were translated into percent strontium released. As the total calculated recovery of strontium from the films generally differed somewhat from 100%, the results were normalized to 100% total release, the films having been totally degraded.

To ensure that no other component of the films absorbed at the strontium absorption wavelength, a number of blank formulations without strontium were prepared in parallel with the strontium formulations and films were made in an identical manner. Then for the in vitro release experiments, parallel experiments on squares of the blank films were carried out as well and the samples read by atomic absorption after dilutions similar to those of the positive samples. The readings were zero in every instance, and after a number of such experiments, the preparation of blank films was discontinued.

EXAMPLE 15

The strontium-release and degradation profiles for the array of formulations tested are shown graphically in FIGS. 12-18. Accompanying each figure or pair of figures is a table detailing the composition of the relevant films, expressed as weight percent of the components. It should be noted that these values include water of crystallization of hydrated salts, which was found to be retained in the dried films. In fact, the films contained 0-10% additional entrapped water, as revealed by their dry weights which were generally slightly higher than calculated from the weights of the components. This additional water has not been taken into account for the composition data.

Figure 12:
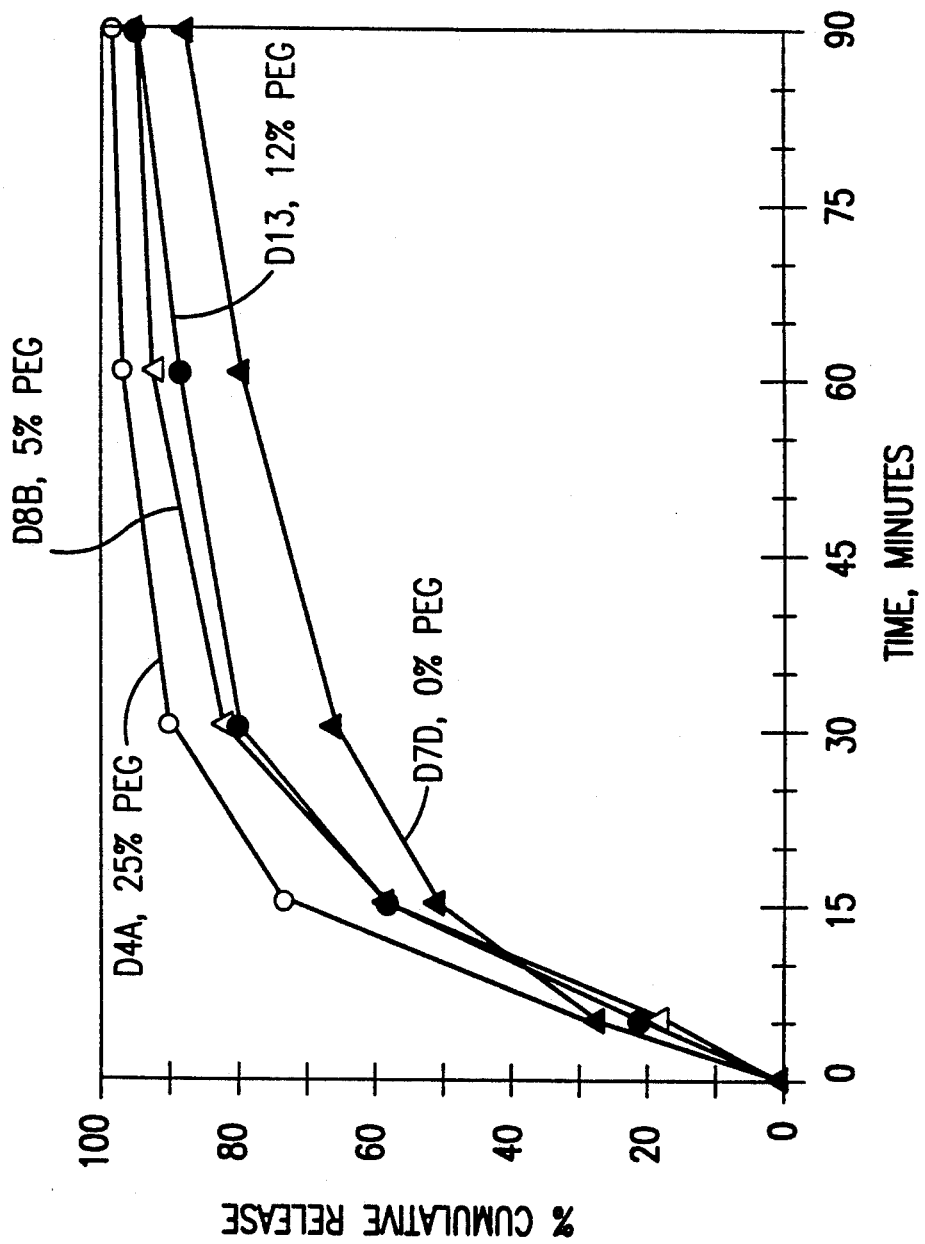
FIG. 12 shows the effect of polyethylene glycol ("PEG") on the release of strontium chloride from a film produced by the drying of a varnish composition. No additives were used.
Figure 13:
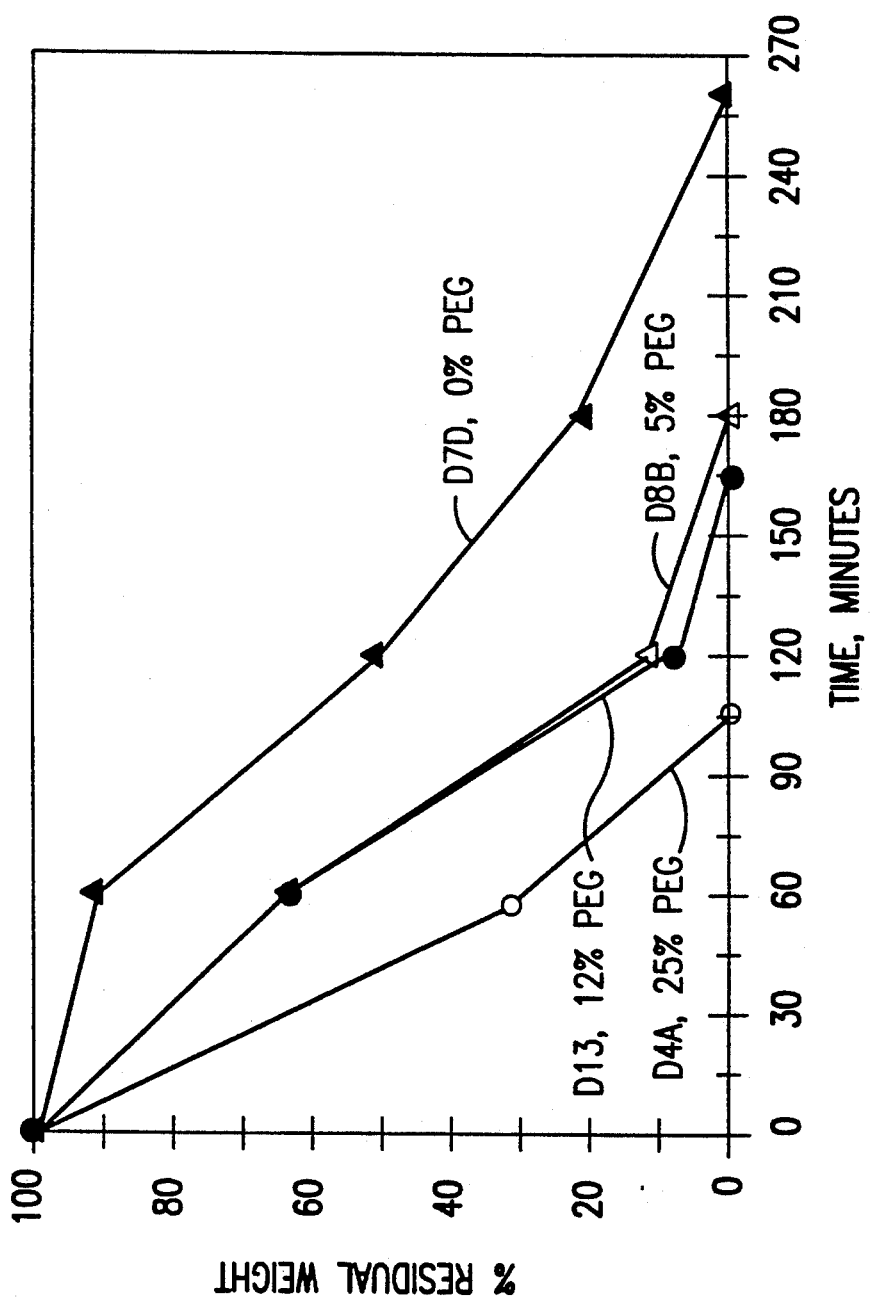
FIG. 13 shows the effect of polyethylene glycol ("PEG") on the degradation of 4 films produced by the drying of a varnish composition. No additives were used.

Films containing only the polymer, strontium chloride and various concentrations of PEG 400 released 50-70% of the strontium in the first 15 minutes (FIG. 12) while it took between 1.5 and 4 hours for the films to be totally degraded (FIG. 13). The composition of these films is shown in Table XIII.

TABLE XIII

| Component | Weight % of Components of Film | | | |
|---|---|---|---|---|
| | D4A | D13 | D8B | D7D |
| Strontium Chloride Hexahydrate | 10 | 10 | 10 | 10 |
| EUDRAGIT L | 65 | 78 | 85 | 90 |
| PEG 400 | 25 | 12 | 5 | — |
| Trisodium Citrate Dihydrate | — | — | — | — |
| Calcium Chloride Dihydrate | — | — | — | — |

The different time scales of the two graphs should be noted. The rates of both strontium release and degradation increase with increasing concentrations of the plasticizer.

Figure 14:
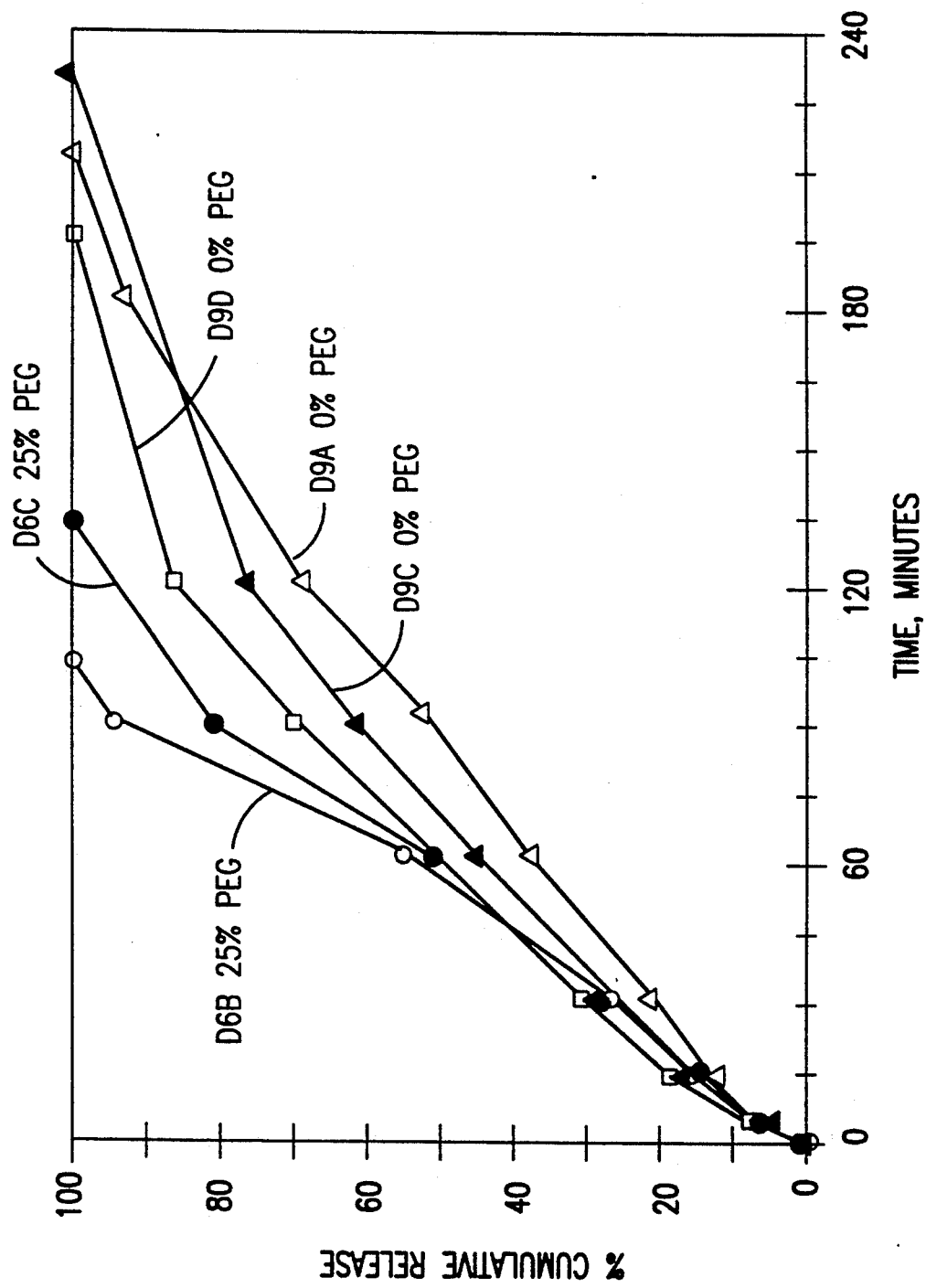
FIG. 14 shows the effect of trisodium citrate on the ability of a film to release strontium.

The addition of 7.4% trisodium citrate to the films dramatically reduced the rate of strontium release (FIG. 14). The composition of these films is shown in Table XIV.

TABLE XIV

| Component | Weight % of Components of Film | |
|---|---|---|
| | D6 | D9 |
| Strontium Chloride Hexahydrate | 10 | 10 |
| EUDRAGIT L | 57.6 | 82.6 |
| PEG 400 | 25 | — |
| Trisodium Citrate Dihydrate | 7.4 | 7.4 |
| Calcium Chloride Dihydrate | — | — |

Almost linear, zero-order kinetics prevail with only 13-19% release in the first 15 minutes. FIG. 14 also illustrates the range of results from replicate in vitro release experiments. Both replicate squares from the same film and squares from replicate films were tested, and replicates were neither prepared nor tested on the same day.

Figure 15:
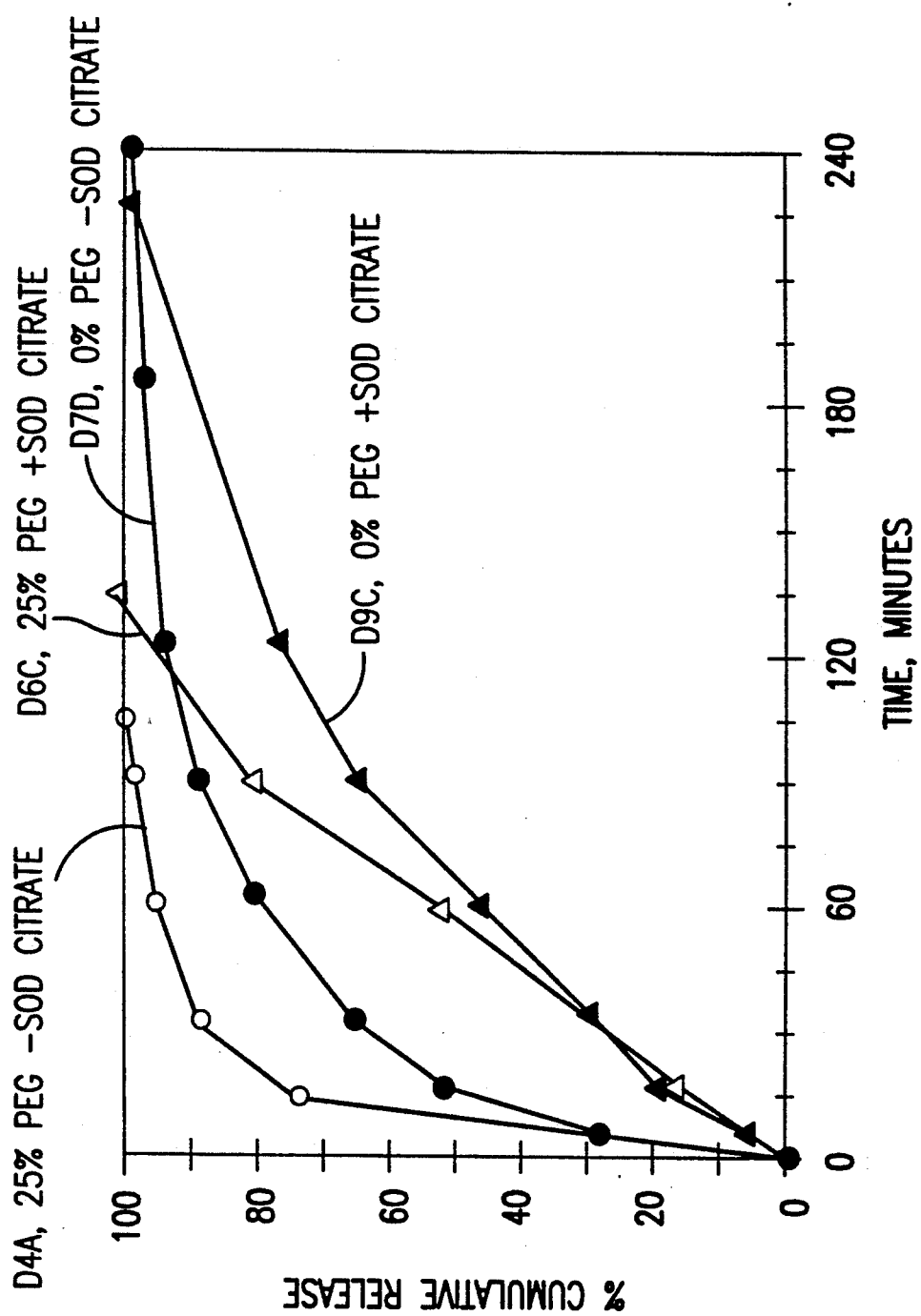
FIG. 15 highlights the effect of the addition of trisodium citrate and also shows that the inclusion of PEG increased the rate of strontium release from citrate-containing films as it did for films without citrate.
Figure 16:
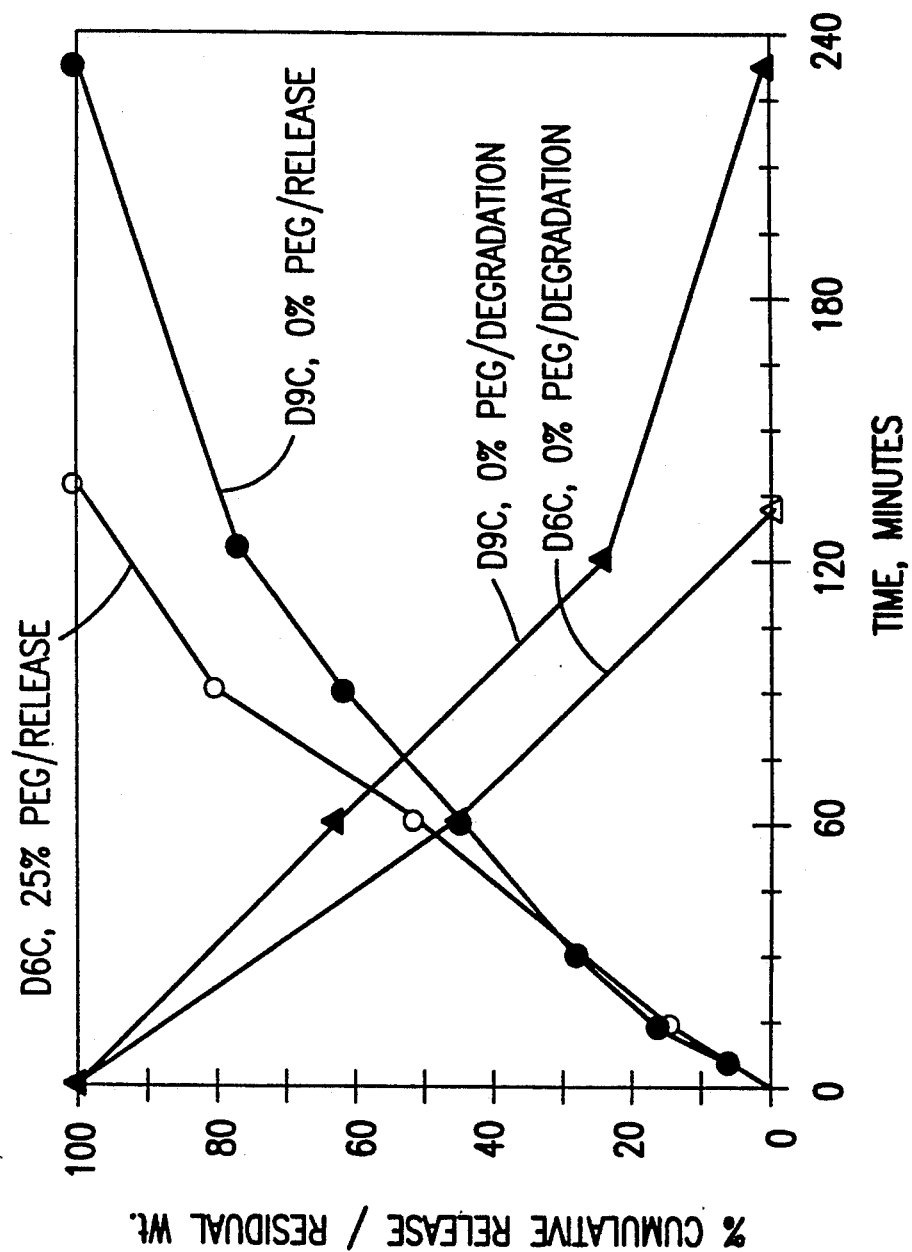
FIG. 16 shows strontium release and degradation of films with sodium citrate and that the degradation rate of a film was increased by PEG, but appeared to be unaffected by trisodium citrate.

FIG. 15 highlights the effect of the addition of trisodium citrate and also shows that the inclusion of PEG increased the rate of strontium release from citrate-containing films as it did for films without citrate. The degradation rate was similarly increased by PEG (FIG. 16), but appeared to be unaffected by trisodium citrate. The composition of these films is shown in Table XV.

TABLE XV

| Component | Weight % of Components of Film | | | |
|---|---|---|---|---|
| | D4A | D7D | D6C | D9C |
| Strontium Chloride Hexahydrate | 10 | 10 | 10 | 10 |
| EUDRAGIT L | 65 | 90 | 57.6 | 82.6 |
| PEG 400 | 25 | — | 25 | — |
| Trisodium Citrate Dihydrate | — | — | 7.4 | 7.4 |
| Calcium Chloride Dihydrate | — | — | — | — |

The symmetry between the release and degradation profiles of films with trisodium citrate (FIG. 16) indicates that the strontium was released steadily over the entire period of degradation of these films, quite different from the behavior of films without citrate (FIGS. 12 and 13).

Figure 17:
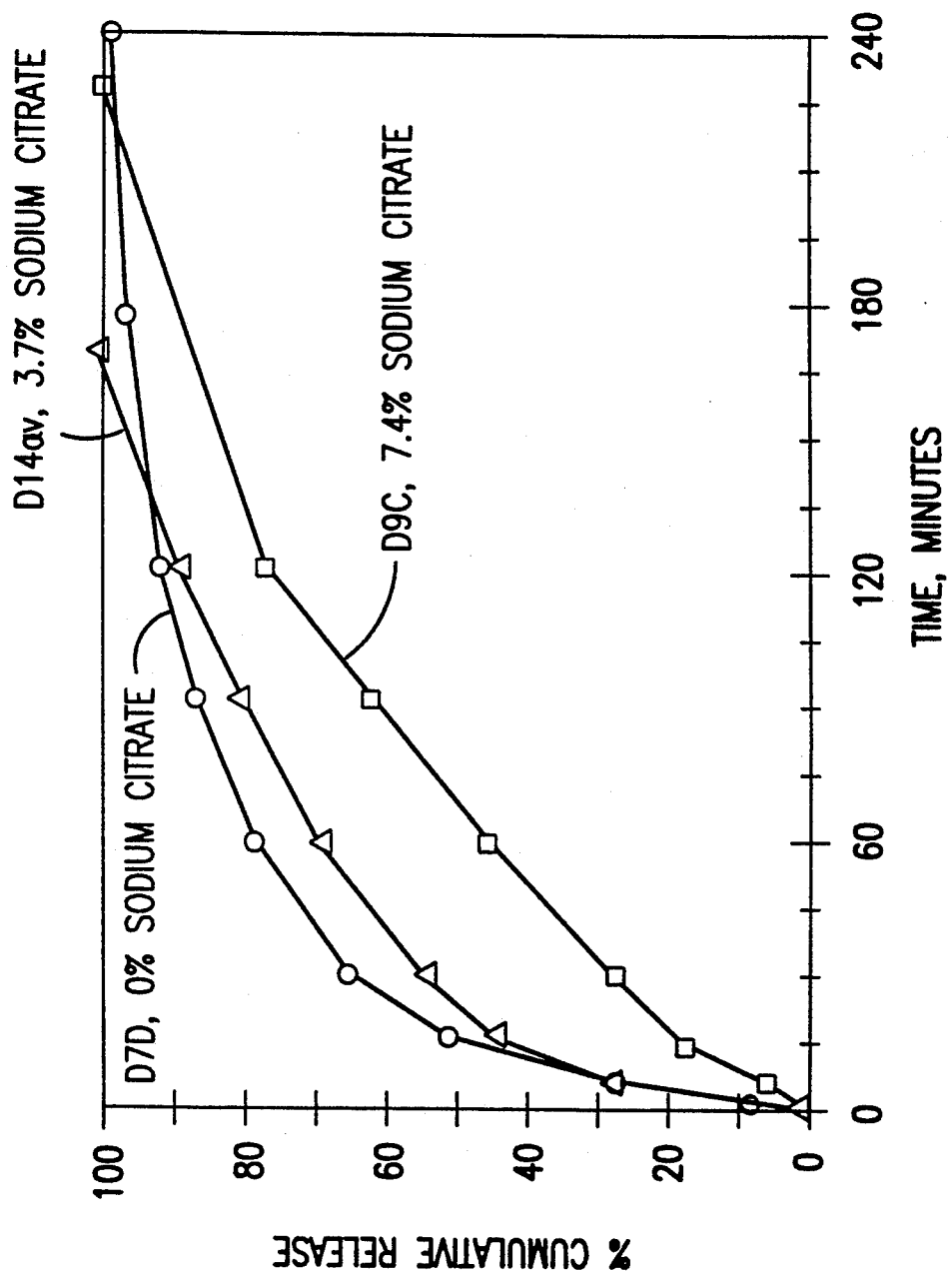
FIG. 17 shows the effect of the concentration of trisodium citrate in a film on the strontium release profile.
Figure 18:
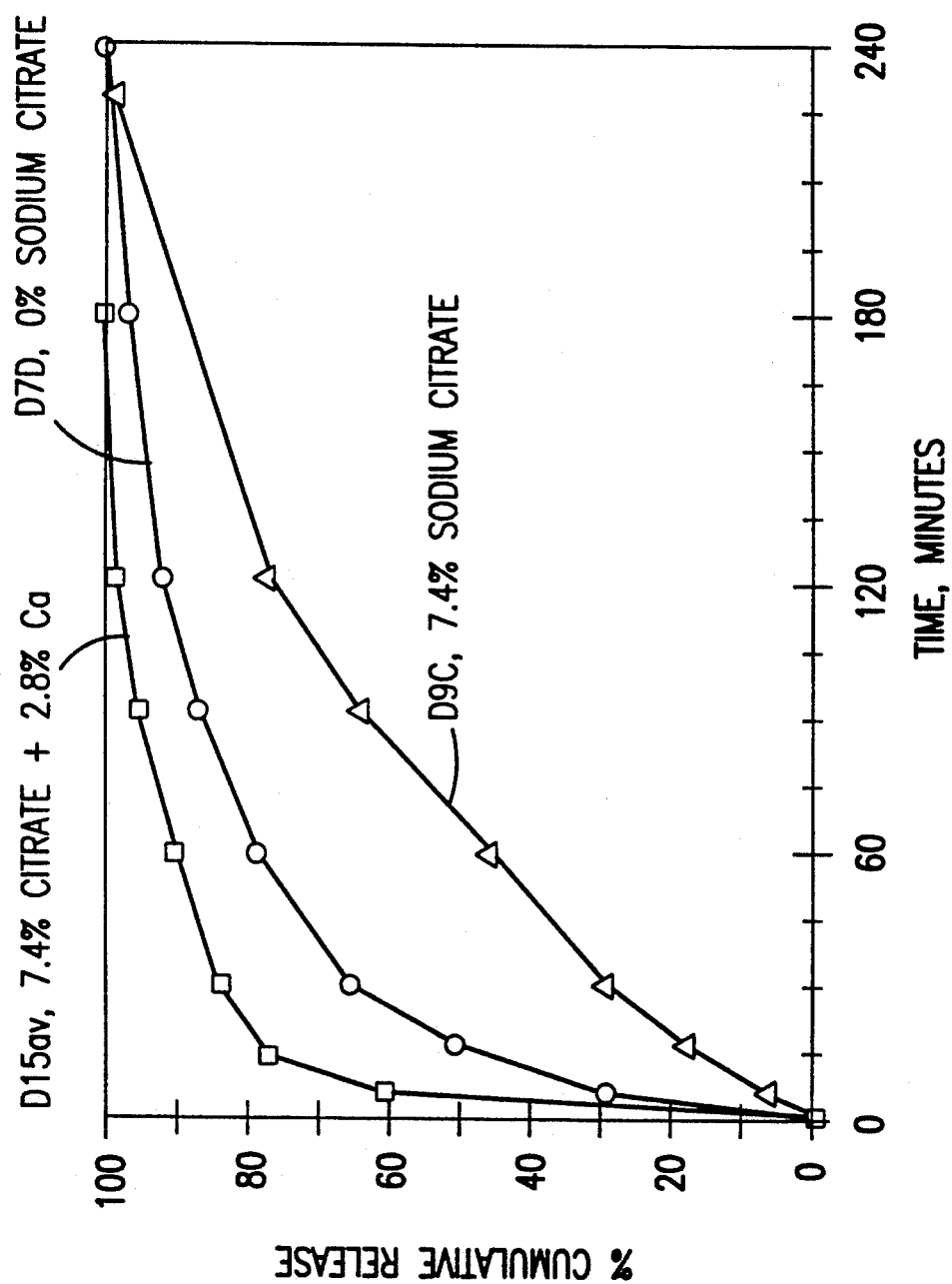
FIG. 18 shows the effect of the concentration of trisodium citrate in a film which additionally contains calcium chloride on the strontium release profile.

When the concentration of trisodium citrate in the film was reduced to half, a strontium release profile of intermediate rate was obtained (FIG. 17). The opposite effect was displayed by a formulation containing calcium chloride in addition to trisodium citrate. The initial release rate was even faster than films without additives, reaching 60% in the first 5 minutes (FIG. 18). No effect on the degradation profile was observed for either additive. The composition of these films is shown in Table XVI.

TABLE XVI

| Component | Weight % of Components of Film | | | |
|---|---|---|---|---|
| | D7D | D14av | D9C | D15av |
| Strontium Chloride Hexahydrate | 10 | 10 | 10 | 10 |
| EUDRAGIT L | 90 | 86.3 | 82.6 | 79.8 |
| PEG 400 | — | — | — | — |
| Trisodium Citrate Dihydrate | — | 3.7 | 7.4 | 7.4 |
| Calcium Chloride Dihydrate | — | — | — | 2.8 |

EXAMPLE 16

The introduction of strontium chloride into a matrix of EUDRAGIT L without additives imparts a limited measure of sustained release. Initial release is rapid, however, and appears to be diffusion controlled, being much faster than the dissolution of the polymer. This increased rates of release and degradation when polyethylene glycol is added to the formulation are possibly due to its action as a plasticizer, increasing the separation between layers of the polymer and thus allowing easier penetration of the buffer.

A different mechanism may be responsible for the zero order release kinetics observed in the presence of 7.4% trisodium citrate. At this concentration the divalent strontium ions in the formulation are exactly balanced by two equivalents of carboxyl groups, and indeed, the appearance of a voluminous precipitate in the formulation on addition of the citrate implicates the formation of strontium citrate (or more precisely tris-trontium dicitrate), which is only slightly soluble. Being a larger molecule than strontium chloride, strontium citrate may be effectively entrapped within the polymer and its low solubility may further limit its ability to diffuse out until the polymer surrounding it dissolves. An alternative explanation is that the divalent strontium ions are linked on one side to citrate carboxyl groups and on the other side to carboxyl groups of the polymer and as such can only enter solution together with the polymer.

The difference between the mechanisms of strontium release with and without sodium citrate was further highlighted by in vitro release experiments done in pure water, which does not dissolve the polymer. Without sodium citrate a release profile similar to that in buffer was observed. In the presence of sodium citrate, however, 12% of the strontium in the film square was released within the first half hour and only a further 1% subsequently; the remaining 87% was not released at all. The small proportion released was either non-entrapped strontium on the surface of the film or free strontium not bound to the polymer. Hence, the rates of release and degradation of films containing 7.4% sodium citrate may be similar (FIG. 16) because the former is dependent on the latter and is controlled by it.

If strontium is bound to the polymer in the film, the possibility was considered that it remains bound after dissolution of the polymer and as such would not be effective for the treatment of hypersensitive teeth. This was discounted by dialysis of dissolved citrate-containing films against the same buffer. After 48 hours and one change of buffer, atomic absorption revealed only 0.1% of the strontium remaining in the polymer solutions. Thus even if the strontium is bound to the polymer in the dry film, it is released as free ionic strontium and ought to be therapeutically effective.

The addition of 2.8% calcium chloride, half the molar quantity of the strontium chloride, to citrate-containing films was expected to increase the release rate by competition with strontium for the available citrate, giving a release profile similar to that from the film with half the quantity of sodium citrate (FIG. 17). The result, however, was surprising (FIG. 18). Calcium appears to expel strontium from citrate-containing films at a rate faster even than the release of strontium from films containing no citrate or calcium.

In conclusion, the film D9 (containing strontium chloride hexahydrate, EUDRAGIT L, and trisodium citrate dehydrate) is the preferred anti-hypersensitivity composition of the present invention, releasing strontium and being degraded steadily over 3-4 hours. Although this formulation contains a precipitate, it settles only slightly over a period of a few days. If a slightly faster initial release is desired, the amount of trisodium citrate can be reduced (as in film D14), or if the degradation in vivo is found to be too prolonged, polyethylene glycol may be added (as in film D6). The precipitates in D6 and D14 settled within one day, but it should be possible to prolong settling by an increase in the viscosity of the formulation (reduction of the solvent volume) or by the addition of a suitable detergent.

EXAMPLE 17

Potassium ion has been used in a variety of dentifrice formulations designated to treat dentin hypersensitivity. The compositions of two anti-hypersensitivity compositions are shown in Table XVII. Composition 1 contains a plasticizer which also acts as an ionic surfactant forming a homogeneous potassium phase. Composition 2 contains an ion-pair agent, which is a relatively water insoluble substance.

TABLE XVII

|  | Composition (% w/w) | |
| --- | --- | --- |
|  | 1 | 2 |
| Potassium Chloride | 2.25 | — |
| Potassium Hydrogen Tartrate | — | 4.5 |
| Methacrylic acid copolymer | 18.02 | 18.02 |
| Sodium docusate | 2.25 | — |
| Alcohol | 50.45 | 50.45 |
| Water | 27.03 | 27.03 |

EXAMPLE 18

The ability of the anti-plaque varnish of the present invention to prevent or attenuate the accumulation of plaque on tooth surfaces was evaluated using 50 human volunteers. The teeth of the volunteers were cleaned (by scaling) to remove accumulated plaque. The volunteers were then divided into two groups. One group received daily treatment with formula MM66 CPC-containing, anti-plaque varnish (discussed in Example 13); the other group received daily treatment with a placebo. At various times after the scaling, the teeth of the volunteers were examined and the plaque indices (PI) of the tooth surface were ascertained. A low PI value indicates less plaque accumulation than a higher PI value. The results of this experiment are shown in Table XVIII.

TABLE XVIII

| Time in Days | Percent of Tooth Surface[1] Scored as: | | | |
| --- | --- | --- | --- | --- |
|  | PI = 0 | | PI = 3 | |
|  | Active | Placebo | Active | Placebo |
| 0[2] | 12.1 | 10.6 | 31.4 | 27.3 |
| 8 | 38.7 | 27.0 | 6.8 | 6.4 |
| 22 | 45.2 | 22.2 | 11.4 | 17.6 |
| 26 | 49.3 | 32.1 | 6.2 | 13.1 |

[1]Distal, mesial, buccal, lingual, and palatial surfaces on the anterior teeth were scored.
[2]Day of scaling; PI determined prior to scaling

Having now fully described the invention, it will be understood by those with skill in the art that the scope may be performed with a wide and equivalent range of conditions, parameters, and the like, without affecting the spirit or scope of the invention or any embodiment thereof.

What is claimed is:

1. A sustained release liquid varnish composition which consists essentially of:
 (a) a sustained release acrylic polymer; and
 (b) either (i) a bacteriocidal quaternary ammonium salt or (ii) a hypersensitivity agent;
in a pharmaceutically acceptable vehicle, wherein said sustained release acrylic polymer is selected from the group consisting of (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, and wherein the concentration of the copolymers in the liquid varnish is 9.9% or greater.

2. The varnish composition of claim 1, wherein said sustained release acrylic polymer is an anionic copolymer based on methacrylic acid and methylmethacrylate wherein the ratio of free carboxyl groups to ester groups is approximately 1:1.

3. The varnish composition of claim 1, wherein said composition contains a bacteriocidal quaternary ammonium salt.

4. The varnish composition of claim 3 wherein said bacteriocidal quaternary ammonium salt is selected from the group consisting of cetylpyridinium chloride and benzalkonium chloride.

5. The varnish composition of claim 4, wherein said bacteriocidal quaternary ammonium salt is cetylpyridinium chloride.

6. The varnish composition of claim 4, wherein said bacteriocidal quaternary ammonium salt is benzalkonium chloride.

7. The varnish composition of claim 1, wherein said composition contains a hypersensitivity agent.

8. The varnish composition of claim 7 wherein said hypersensitivity agent is selected from the group consisting of a strontium salt, and a potassium salt.

9. The varnish composition of claim 8, wherein said strontium salt is selected from the group consisting of strontium chloride and strontium citrate.

10. The varnish composition of claim 8, wherein said potassium salt is selected from the group consisting of potassium chloride and potassium hydrogen tartrate.

11. The varnish composition of claim 1, wherein said pharmaceutically acceptable vehicle comprises an agent selected from the group consisting of water; ethyl alcohol; and ethyl alcohol and water.

12. A sustained release liquid varnish composition which consists essentially of:
(a) a sustained release acrylic polymer;
(b) either (i) a bacteriocidal quaternary ammonium salt or (ii) a hypersensitivity agent; and
(c) an agent selected form the group consisting of a flavoring agent, and a coloring agent;
in a pharmaceutically acceptable vehicle, wherein said sustained release acrylic polymer is selected from the group consisting of (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, and wherein the concentration of the copolymers in the liquid varnish is 9.9% or greater.

13. A sustained release liquid varnish composition which consists essentially of:
(a) a sustained release acrylic polymer;
(b) either (i) a bacteriocidal quaternary ammonium salt or (ii) a hypersensitivity agent; and
(c) a plasticizer;
in a pharmaceutically acceptable vehicle, wherein said sustained release acrylic polymer is selected from the group consisting of (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, and wherein the concentration of the copolymers in the liquid varnish is 9.9% or greater.

14. A sustained release liquid varnish composition which consists essentially of:
(a) a sustained release acrylic polymer;
(b) either (i) a bacteriocidal quaternary ammonium salt or (ii) a hypersensitivity agent; and
(c) an agent selected from the group consisting of: polyethylene glycol and dibutyl phthalate;
in a pharmaceutically acceptable vehicle, wherein said sustained release acrylic polymer is selected from the group consisting of (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, and wherein the concentration of the copolymers in the liquid varnish is 9.9% or greater.

15. A method of treating tooth hypersensitivity comprising application of the varnish composition of claim 7 to the teeth or gingival tissues of an animal.

16. A method of oral plaque prevention comprising application of the varnish composition of claim 3 to the teeth or gingival tissues of an animal.

17. The method of claim 16, wherein said application is by brush.

18. The method of claim 16, wherein said application is by spray.

19. The method of claim 16, wherein said animal is a human.

20. The method of claim 16, wherein said animal is a domesticated animal.

21. The method of claim 15, wherein said animal is a domesticated animal.

22. The method of claim 15, wherein said application is by brush.

23. The method of claim 15, wherein said application is by spray.

24. The method of claim 15, wherein said animal is a human.

* * * * *

UNITED STATES PATENT AND TRADEMARK OFFICE
CERTIFICATE OF CORRECTION

PATENT NO. : 5,330,746
DATED : July 19, 1994
INVENTOR(S) : Friedman et al.

It is certified that error appears in the above-identified patent and that said Letters Patent is hereby corrected as shown below:

<u>Title page,</u>
Item [73], please delete "Petro Products Ltd." and insert therein -- Perio Products Ltd. --.

Signed and Sealed this

Twenty-sixth Day of February, 2002

*Attest:*

JAMES E. ROGAN
*Attesting Officer   Director of the United States Patent and Trademark Office*